US010617653B2

(12) United States Patent
Armbruster et al.

(10) Patent No.: US 10,617,653 B2
(45) Date of Patent: Apr. 14, 2020

(54) FILMS AND METHODS OF MANUFACTURE

(71) Applicant: DePuy Synthes Products, Inc., Raynham, MA (US)

(72) Inventors: David Armbruster, West Chester, PA (US); James Dwyer, West Chester, PA (US); Jeffrey Chomyn, Murrieta, CA (US); Sean Kerr, Oreland, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 325 days.

(21) Appl. No.: 15/177,687

(22) Filed: Jun. 9, 2016

(65) Prior Publication Data

US 2016/0287527 A1 Oct. 6, 2016

Related U.S. Application Data

(62) Division of application No. 13/727,682, filed on Dec. 27, 2012, now Pat. No. 9,381,683.

(Continued)

(51) Int. Cl.
*A61K 9/70* (2006.01)
*B29C 39/02* (2006.01)
(Continued)

(52) U.S. Cl.
CPC ............ *A61K 9/7007* (2013.01); *A61B 17/70* (2013.01); *A61B 17/80* (2013.01);
(Continued)

(58) Field of Classification Search
None
See application file for complete search history.

(56) References Cited

U.S. PATENT DOCUMENTS 3,155,095 A 11/1964 Brown
3,719,736 A 3/1973 Woodruf
(Continued)

FOREIGN PATENT DOCUMENTS

AU 2004/202878 12/2005
CN 1206353 A 1/1999
(Continued)

OTHER PUBLICATIONS

U.S. Appl. No. 60/726,808, filed Oct. 13, 2005, Kerr et al.
(Continued)

*Primary Examiner* — Francisco W Tschen
(74) *Attorney, Agent, or Firm* — BakerHostetler

(57) ABSTRACT

A flexible body comprises a polymer film having a first surface and an opposing second surface. The polymer film has a plurality of apertures extending from the first surface to the second surface and a plurality of raised lips protruding from the first surface such that each of the plurality of apertures is surrounded by one of the plurality of raised lips. A method of producing a polymer film comprises placing a polymer solution into a one sided mold having a plurality of protrusions extending from a bottom of the mold wherein the polymer solution is characterized by a viscosity that inhibits the unaided flow of the polymer throughout the mold; urging the polymer solution around each of the plurality of protrusions; and solidifying the polymer solution.

21 Claims, 16 Drawing Sheets

Related U.S. Application Data

(60) Provisional application No. 61/580,679, filed on Dec. 28, 2011.

(51) Int. Cl.
| | |
|---|---|
| *B29C 39/00* | (2006.01) |
| *B29C 39/24* | (2006.01) |
| *B29C 39/26* | (2006.01) |
| *A61L 27/18* | (2006.01) |
| *A61L 27/50* | (2006.01) |
| *A61L 27/54* | (2006.01) |
| *A61K 9/00* | (2006.01) |
| *A61B 17/70* | (2006.01) |
| *A61B 17/80* | (2006.01) |
| *B29D 7/01* | (2006.01) |
| *B29C 41/02* | (2006.01) |
| *C08J 5/18* | (2006.01) |
| *A61K 31/085* | (2006.01) |
| *A61K 31/7036* | (2006.01) |
| *B29C 39/38* | (2006.01) |
| *A61F 2/30* | (2006.01) |
| *A61F 2/28* | (2006.01) |
| *C08L 69/00* | (2006.01) |
| *A61F 2/02* | (2006.01) |
| *C08L 67/04* | (2006.01) |
| *A61F 2/00* | (2006.01) |
| *A61F 13/00* | (2006.01) |
| *A61B 17/00* | (2006.01) |
| *A61B 17/56* | (2006.01) |
| *B29K 67/00* | (2006.01) |
| *A61M 31/00* | (2006.01) |
| *B29K 105/00* | (2006.01) |
| *B29L 7/00* | (2006.01) |
| *B29L 31/00* | (2006.01) |

(52) U.S. Cl.
CPC ........ *A61B 17/8028* (2013.01); *A61K 9/0024* (2013.01); *A61K 31/085* (2013.01); *A61K 31/7036* (2013.01); *A61L 27/18* (2013.01); *A61L 27/50* (2013.01); *A61L 27/54* (2013.01); *B29C 39/003* (2013.01); *B29C 39/026* (2013.01); *B29C 39/24* (2013.01); *B29C 39/26* (2013.01); *B29C 39/38* (2013.01); *B29C 41/02* (2013.01); *B29D 7/01* (2013.01); *C08J 5/18* (2013.01); *A61B 2017/00004* (2013.01); *A61B 2017/00526* (2013.01); *A61B 2017/561* (2013.01); *A61F 2/0063* (2013.01); *A61F 2/0077* (2013.01); *A61F 2/02* (2013.01); *A61F 2/28* (2013.01); *A61F 2/2846* (2013.01); *A61F 2/30907* (2013.01); *A61F 2002/30062* (2013.01); *A61F 2002/30064* (2013.01); *A61F 2002/30067* (2013.01); *A61F 2002/30069* (2013.01); *A61F 2002/30919* (2013.01); *A61F 2013/00221* (2013.01); *A61F 2013/00357* (2013.01); *A61F 2210/0004* (2013.01); *A61F 2250/0031* (2013.01); *A61F 2250/0067* (2013.01); *A61L 2300/604* (2013.01); *A61M 31/002* (2013.01); *B29K 2067/04* (2013.01); *B29K 2067/043* (2013.01); *B29K 2067/046* (2013.01); *B29K 2105/0002* (2013.01); *B29K 2105/0035* (2013.01); *B29K 2105/0073* (2013.01); *B29K 2995/006* (2013.01); *B29L 2007/008* (2013.01); *B29L 2031/753* (2013.01); *C08J 2367/04* (2013.01); *C08J 2369/00* (2013.01); *C08L 67/04* (2013.01); *C08L 69/005* (2013.01); *Y10S 525/937* (2013.01); *Y10T 428/24182* (2015.01); *Y10T 428/24281* (2015.01); *Y10T 428/24479* (2015.01); *Y10T 428/25* (2015.01); *Y10T 428/26* (2015.01)

(56) References Cited

U.S. PATENT DOCUMENTS

| | | | |
|---|---|---|---|
| 3,949,037 A * | 4/1976 | Volent | B44F 11/06 |
| | | | 264/129 |
| 4,148,871 A | 4/1979 | Pitt et al. | |
| 4,297,993 A | 11/1981 | Harle | |
| 4,587,268 A | 5/1986 | Pfirrmann | |
| 4,605,414 A | 8/1986 | Czajka | |
| 4,605,730 A | 8/1986 | Shalaby et al. | |
| 4,659,700 A | 4/1987 | Jackson | |
| 4,730,726 A | 3/1988 | Holzwarth | |
| 4,774,091 A | 9/1988 | Yamahira et al. | |
| 4,863,444 A | 9/1989 | Biomer | |
| 4,888,023 A | 12/1989 | Averill et al. | |
| 5,021,241 A | 6/1991 | Yamahira et al. | |
| 5,084,050 A | 1/1992 | Draenert | |
| 5,093,319 A | 3/1992 | Higham et al. | |
| 5,100,668 A | 3/1992 | Edelman | |
| 5,104,266 A | 4/1992 | Daryoush | |
| 5,147,400 A | 9/1992 | Kaplan et al. | |
| 5,260,066 A * | 11/1993 | Wood | A61K 9/2027 |
| | | | 424/443 |
| 5,268,178 A | 12/1993 | Calhoun et al. | |
| 5,281,221 A | 1/1994 | Tadych | |
| 5,324,519 A | 6/1994 | Dunn et al. | |
| 5,326,356 A | 7/1994 | Della Valle et al. | |
| 5,383,928 A | 1/1995 | Scott | |
| 5,456,721 A | 10/1995 | Legrand | |
| 5,458,653 A | 10/1995 | Davidson | |
| 5,462,563 A | 10/1995 | Shearer | |
| 5,468,253 A | 11/1995 | Bezwada | |
| 5,489,305 A | 2/1996 | Morgan | |
| 5,507,814 A | 4/1996 | Gilbert | |
| 5,521,193 A | 5/1996 | Flynn | |
| 5,549,676 A | 8/1996 | Johnson | |
| 5,567,431 A | 10/1996 | Vert et al. | |
| 5,571,204 A | 11/1996 | Nies | |
| 5,637,113 A | 6/1997 | Tartaglia et al. | |
| 5,656,605 A | 8/1997 | Hansson | |
| 5,679,299 A | 10/1997 | Gilbert et al. | |
| 5,693,085 A | 12/1997 | Buirge et al. | |
| 5,713,904 A | 2/1998 | Errico et al. | |
| 5,716,981 A | 2/1998 | Hunter et al. | |
| 5,725,570 A | 3/1998 | Heath | |
| 5,755,720 A | 5/1998 | Mikhail | |
| 5,795,584 A | 8/1998 | Totakura et al. | |
| 5,798,113 A | 8/1998 | Dionne et al. | |
| 5,800,519 A | 9/1998 | Sandock | |
| 5,800,544 A | 9/1998 | Demopulos et al. | |
| 5,800,828 A | 9/1998 | Dionne | |
| 5,800,829 A | 9/1998 | Dionne et al. | |
| 5,824,088 A | 10/1998 | Kirsch | |
| 5,834,001 A | 10/1998 | Dionne et al. | |
| 5,855,906 A | 1/1999 | McClay | |
| 5,869,077 A | 2/1999 | Dionne et al. | |
| 5,871,767 A | 2/1999 | Dionne et al. | |
| 5,873,906 A | 2/1999 | Lave et al. | |
| 5,874,099 A | 2/1999 | Dionne et al. | |
| 5,876,432 A | 3/1999 | Lau et al. | |
| 5,919,225 A | 7/1999 | Lau et al. | |
| 5,919,235 A | 7/1999 | Husson et al. | |
| 5,947,893 A | 9/1999 | Agrawal et al. | |
| 5,955,095 A | 9/1999 | Gentile et al. | |
| 5,984,926 A | 11/1999 | Jones | |
| 6,001,123 A | 12/1999 | Lau et al. | |
| 6,013,104 A | 1/2000 | Kampner | |
| 6,015,429 A | 1/2000 | Lau et al. | |
| 6,017,362 A | 1/2000 | Lau | |
| 6,060,640 A * | 5/2000 | Pauley | A61F 2/022 |
| | | | 623/1.41 |
| 6,063,395 A | 5/2000 | Markkula | |

(56) References Cited

U.S. PATENT DOCUMENTS

| | | |
|---|---|---|
| 6,071,567 A | 6/2000 | Castelli et al. |
| 6,083,523 A | 7/2000 | Dionne et al. |
| 6,117,442 A | 9/2000 | Markkula et al. |
| 6,143,029 A | 11/2000 | Rippstein |
| 6,143,033 A | 11/2000 | Paul et al. |
| 6,165,202 A | 12/2000 | Kokish et al. |
| 6,165,210 A | 12/2000 | Lau |
| 6,180,052 B1 | 1/2001 | Ouellette et al. |
| 6,193,746 B1 | 2/2001 | Strecker |
| 6,221,097 B1 | 4/2001 | Wang et al. |
| 6,232,869 B1 | 5/2001 | Roby et al. |
| 6,235,869 B1 | 5/2001 | Roby et al. |
| 6,248,112 B1 | 6/2001 | Gambale et al. |
| 6,254,627 B1 | 7/2001 | Friedberg |
| 6,258,125 B1 | 7/2001 | Paul et al. |
| 6,277,084 B1 | 8/2001 | Abele |
| 6,280,411 B1 | 8/2001 | Lennox |
| 6,287,291 B1 | 9/2001 | Bigus |
| 6,287,331 B1 | 9/2001 | Heath |
| 6,287,628 B1 | 9/2001 | Hossainy et al. |
| 6,287,638 B1 | 9/2001 | Castelli et al. |
| 6,290,721 B1 | 9/2001 | Heath |
| 6,299,894 B1 | 10/2001 | Markkula |
| 6,306,166 B1 | 10/2001 | Barry |
| 6,322,804 B1 | 11/2001 | Dionne et al. |
| 6,331,186 B1 | 12/2001 | Wang et al. |
| 6,331,188 B1 | 12/2001 | Lau et al. |
| 6,337,088 B1 | 1/2002 | Gentile et al. |
| 6,350,284 B1 | 2/2002 | Tormaia |
| 6,379,381 B1 | 4/2002 | Hossainy et al. |
| 6,383,190 B1 | 5/2002 | Preissman |
| 6,419,694 B1 | 7/2002 | Sandock |
| 6,432,141 B1 | 8/2002 | Stocks et al. |
| 6,443,980 B1 | 9/2002 | Wang et al. |
| 6,447,522 B2 | 9/2002 | Gambale et al. |
| 6,451,003 B1 | 9/2002 | Prosl et al. |
| 6,451,050 B1 | 9/2002 | Rudakov et al. |
| 6,468,300 B1 | 10/2002 | Freidberg |
| 6,476,079 B1 | 11/2002 | Jukarainen et al. |
| 6,482,235 B1 | 11/2002 | Lambrecht et al. |
| 6,491,720 B1 | 12/2002 | Vallana et al. |
| 6,494,898 B1 | 12/2002 | Roby et al. |
| 6,497,709 B1 | 12/2002 | Heath |
| 6,503,556 B2 | 1/2003 | Harish et al. |
| 6,503,954 B1 | 1/2003 | Bhat et al. |
| 6,517,570 B1 | 2/2003 | Lau et al. |
| 6,520,984 B1 | 2/2003 | Garrison et al. |
| 6,545,097 B2 | 4/2003 | Pinchuk et al. |
| 6,547,812 B1 | 4/2003 | Hu |
| 6,554,863 B2 | 4/2003 | Paul et al. |
| 6,569,180 B1 | 5/2003 | Sirhan et al. |
| 6,592,569 B2 | 7/2003 | Bigus et al. |
| 6,592,885 B2 | 7/2003 | Phaneuf et al. |
| 6,596,296 B1 | 7/2003 | Nelson et al. |
| 6,602,290 B2 | 8/2003 | Esnouf et al. |
| 6,607,544 B1 | 8/2003 | Boucher et al. |
| 6,613,072 B2 | 9/2003 | Lau et al. |
| 6,632,235 B2 | 10/2003 | Weikel et al. |
| 6,641,587 B2 | 11/2003 | Scribner et al. |
| 6,645,241 B1 | 11/2003 | Strecker |
| 6,660,038 B2 | 12/2003 | Boyer, II et al. |
| 6,666,880 B1 | 12/2003 | Chiu et al. |
| 6,692,498 B1 | 2/2004 | Niiranen et al. |
| 6,706,058 B2 | 3/2004 | Hierlemann et al. |
| 6,713,119 B2 | 3/2004 | Hossainy et al. |
| 6,716,216 B1 | 4/2004 | Boucher et al. |
| 6,716,444 B1 | 4/2004 | Castro |
| 6,719,773 B1 | 4/2004 | Boucher et al. |
| 6,726,691 B2 | 4/2004 | Osorio et al. |
| 6,746,483 B1 | 6/2004 | Bojarski et al. |
| 6,749,626 B1 | 6/2004 | Bhat et al. |
| 6,759,054 B2 | 7/2004 | Chen et al. |
| 6,767,369 B2 | 7/2004 | Boyer, II et al. |
| 6,790,224 B2 | 9/2004 | Gerberding |
| 6,790,228 B2 | 9/2004 | Hossainy et al. |
| RE38,614 E | 10/2004 | Paul et al. |
| 6,818,247 B1 | 11/2004 | Chen et al. |
| 6,827,743 B2 | 12/2004 | Eisermann et al. |
| 6,840,770 B2 | 1/2005 | McDevitt |
| 6,855,770 B2 | 2/2005 | Pinchuk |
| 6,863,530 B2 | 3/2005 | McDevitt |
| 6,863,692 B2 | 3/2005 | Meulink |
| 6,883,520 B2 | 4/2005 | Lambrecht et al. |
| 6,884,427 B1 | 4/2005 | Barrows |
| 6,899,719 B2 | 5/2005 | Reiley et al. |
| 6,908,624 B2 | 6/2005 | Hossainy |
| 6,946,143 B2 | 9/2005 | Kim et al. |
| 6,953,560 B1 | 10/2005 | Castro et al. |
| 6,960,351 B2 | 11/2005 | Dionne et al. |
| 6,979,341 B2 | 12/2005 | Scribner et al. |
| 6,981,991 B2 | 1/2006 | Ferree |
| 6,986,788 B2 | 1/2006 | Paul et al. |
| 7,001,390 B2 | 2/2006 | Gebhardt |
| 7,014,659 B2 | 3/2006 | Boyer, II et al. |
| 7,025,791 B2 | 4/2006 | Levine et al. |
| 7,037,332 B2 | 5/2006 | Kutryk et al. |
| 7,041,308 B2 | 5/2006 | Shalaby et al. |
| 7,056,577 B1 | 6/2006 | Bruce et al. |
| 7,070,613 B2 | 7/2006 | Weber et al. |
| 7,087,082 B2 | 8/2006 | Paul et al. |
| 7,087,087 B2 | 8/2006 | Boyer et al. |
| 7,101,392 B2 | 9/2006 | Heath |
| 7,108,717 B2 | 9/2006 | Freidberg |
| 7,115,146 B2 | 10/2006 | Boyer, II et al. |
| 7,122,058 B2 | 10/2006 | Levine et al. |
| 7,131,986 B2 | 11/2006 | Sirhan et al. |
| 7,137,993 B2 | 11/2006 | Acosta et al. |
| 7,147,656 B2 | 12/2006 | Andreas et al. |
| 7,153,306 B2 | 12/2006 | Ralph et al. |
| 7,153,307 B2 | 12/2006 | Scribner et al. |
| 7,168,605 B2 | 1/2007 | Walak |
| 7,169,405 B2 | 1/2007 | Trieu |
| 7,175,873 B1 | 2/2007 | Roorda et al. |
| 7,182,779 B2 | 2/2007 | Acosta et al. |
| 7,192,448 B2 | 3/2007 | Ferree |
| 7,198,047 B2 | 4/2007 | Lambrecht et al. |
| 7,208,008 B2 | 4/2007 | Clarke |
| 7,238,168 B2 | 7/2007 | Sirhan et al. |
| 7,247,313 B2 | 7/2007 | Roorda et al. |
| 7,252,671 B2 | 8/2007 | Scribner et al. |
| 7,261,720 B2 | 8/2007 | Stevens et al. |
| 7,267,694 B2 | 9/2007 | Levine et al. |
| 7,270,668 B2 | 9/2007 | Adreas et al. |
| 7,279,008 B2 | 10/2007 | Brown et al. |
| 7,279,175 B2 | 10/2007 | Chen et al. |
| 7,294,146 B2 | 11/2007 | Chew et al. |
| 7,296,998 B2 | 11/2007 | Bartee et al. |
| 7,300,456 B2 | 11/2007 | Andreas et al. |
| 7,300,465 B2 | 11/2007 | Paul et al. |
| 7,309,350 B2 | 12/2007 | Landreville et al. |
| 7,311,727 B2 | 12/2007 | Mazumder et al. |
| 7,329,285 B2 | 2/2008 | Levine et al. |
| 7,347,873 B2 | 3/2008 | Paul et al. |
| 7,347,875 B2 | 3/2008 | Levine et al. |
| 7,351,255 B2 | 4/2008 | Andreas |
| 7,357,812 B2 | 4/2008 | Andreas et al. |
| 7,402,172 B2 | 7/2008 | Chin et al. |
| 7,407,512 B2 | 8/2008 | Bojarski et al. |
| 7,458,990 B2 | 12/2008 | Chieng |
| 7,465,318 B2 | 12/2008 | Sennett et al. |
| 7,473,277 B2 | 1/2009 | Boyer, II et al. |
| 7,491,234 B2 | 2/2009 | Palasis |
| 7,503,936 B2 | 3/2009 | Trieu |
| 7,504,125 B1 | 3/2009 | Pacetti et al. |
| 7,550,012 B2 | 6/2009 | Lavelle |
| 7,553,539 B2 | 6/2009 | Bruce |
| 7,578,834 B2 | 8/2009 | Abdou |
| 7,608,114 B2 | 10/2009 | Levine et al. |
| 7,611,481 B2 | 11/2009 | Cleary et al. |
| 7,618,432 B2 | 11/2009 | Pedersen et al. |
| 7,618,448 B2 | 11/2009 | Schmitz et al. |
| 7,618,647 B2 | 11/2009 | Weber |
| 7,622,146 B2 | 11/2009 | Roorda et al. |
| 7,622,530 B2 | 11/2009 | Pinchuk et al. |

(56) References Cited

U.S. PATENT DOCUMENTS

| | | | |
|---|---|---|---|
| 7,666,216 B2 | 2/2010 | Hogendijk et al. |
| 7,678,068 B2 | 3/2010 | Levine et al. |
| 7,682,647 B2 | 3/2010 | Hossainy et al. |
| 7,686,781 B2 | 3/2010 | Vinten-Johansen |
| 7,691,401 B2 | 4/2010 | Castro et al. |
| 7,695,446 B2 | 4/2010 | Levine et al. |
| 7,698,111 B2 | 4/2010 | Abrahad et al. |
| 7,704,545 B2 | 4/2010 | Kantor et al. |
| 7,731,750 B2 | 6/2010 | Bojarski et al. |
| 7,740,657 B2 | 6/2010 | Brown, Jr. et al. |
| 7,744,620 B2 | 6/2010 | Pedersen et al. |
| 7,758,535 B2 | 7/2010 | Levine et al. |
| 7,758,642 B2 | 7/2010 | Bojarski et al. |
| 7,758,881 B2 | 7/2010 | Dugan |
| 7,766,861 B2 | 8/2010 | Levine et al. |
| 7,766,973 B2 | 8/2010 | Levine et al. |
| 7,771,382 B2 | 8/2010 | Levine et al. |
| 7,785,615 B2 | 8/2010 | Dave |
| 7,789,915 B2 | 9/2010 | Lavelle et al. |
| 7,803,183 B2 | 9/2010 | Kutryk et al. |
| 7,988,732 B2 | 2/2011 | Bojarski et al. |
| 8,900,620 B2 | 12/2014 | Fulmer et al. |
| 9,381,683 B2 | 7/2016 | Armbruster et al. |
| 9,579,260 B2 | 2/2017 | Fulmer et al. |
| 2001/0039456 A1 | 11/2001 | Boyer, II et al. |
| 2002/0055749 A1 | 5/2002 | Esnouf et al. |
| 2002/0062147 A1 | 5/2002 | Yang |
| 2002/0187260 A1 | 12/2002 | Sheppard, Jr. et al. |
| 2003/0088307 A1 | 5/2003 | Shulze et al. |
| 2003/0093111 A1 | 5/2003 | Ken et al. |
| 2003/0107149 A1* | 6/2003 | Yang ................ A61K 9/006 |
| | | | 264/134 |
| 2003/0149466 A1 | 8/2003 | Gerberding |
| 2004/0093058 A1 | 5/2004 | Cottone et al. |
| 2004/0093062 A1 | 5/2004 | Glastra |
| 2004/0146546 A1 | 7/2004 | Garrett et al. |
| 2004/0225359 A1 | 11/2004 | Bojarski et al. |
| 2004/0267347 A1 | 12/2004 | Cervantes |
| 2004/0267354 A1* | 12/2004 | Ringeisen ............. A61L 27/18 |
| | | | 623/1.42 |
| 2005/0019404 A1* | 1/2005 | Sung .................. A61F 2/92 |
| | | | 424/468 |
| 2005/0129732 A1 | 6/2005 | Rubsamen |
| 2005/0159805 A1 | 7/2005 | Weber et al. |
| 2005/0181977 A1 | 8/2005 | Hunter et al. |
| 2005/0209629 A1 | 9/2005 | Kerr et al. |
| 2005/0209704 A1 | 9/2005 | Maspero et al. |
| 2005/0246021 A1 | 11/2005 | Ringeisen et al. |
| 2005/0261782 A1 | 11/2005 | Hoganson |
| 2005/0278011 A1 | 12/2005 | Pokeham |
| 2006/0093646 A1 | 5/2006 | Cima et al. |
| 2006/0234061 A1 | 10/2006 | Buckel et al. |
| 2006/0259122 A1 | 11/2006 | Eliseev |
| 2006/0263355 A1 | 11/2006 | Quan et al. |
| 2006/0276906 A1 | 12/2006 | Hoag et al. |
| 2006/0286137 A1 | 12/2006 | Sandhu et al. |
| 2007/0038299 A1 | 2/2007 | Stone et al. |
| 2007/0118211 A1 | 5/2007 | Gazza |
| 2007/0141103 A1 | 6/2007 | Benedict et al. |
| 2007/0142892 A1 | 6/2007 | Dave et al. |
| 2007/0198040 A1 | 8/2007 | Buevich et al. |
| 2007/0213801 A1 | 9/2007 | Kutryk et al. |
| 2007/0255422 A1 | 11/2007 | Wei et al. |
| 2008/0033548 A1 | 2/2008 | Xuenong et al. |
| 2008/0057096 A1 | 3/2008 | Ibsen |
| 2008/0097570 A1 | 4/2008 | Thornton et al. |
| 2008/0107711 A1 | 5/2008 | Shelokov |
| 2008/0112892 A1 | 5/2008 | Veenstra et al. |
| 2008/0125847 A1 | 5/2008 | Krever et al. |
| 2008/0128315 A1 | 6/2008 | Buevich et al. |
| 2008/0132922 A1 | 6/2008 | Buevich et al. |
| 2008/0132992 A1 | 6/2008 | Bates et al. |
| 2008/0195218 A1 | 8/2008 | Jones |
| 2008/0241212 A1 | 10/2008 | Moses et al. |
| 2008/0262630 A1 | 10/2008 | Fulmer et al. |
| 2009/0012595 A1 | 1/2009 | Seliktar et al. |
| 2009/0018640 A1 | 1/2009 | State |
| 2009/0062899 A1 | 3/2009 | Dang et al. |
| 2009/0069904 A1 | 3/2009 | Picha |
| 2009/0076449 A1 | 3/2009 | Geis et al. |
| 2009/0076508 A1 | 3/2009 | Weinans et al. |
| 2009/0081276 A1 | 3/2009 | Aisberg et al. |
| 2009/0081278 A1 | 3/2009 | DeGraaff et al. |
| 2009/0092654 A1 | 4/2009 | de Juan, Jr. et al. |
| 2009/0118817 A1 | 5/2009 | Sandhu et al. |
| 2009/0130167 A1 | 5/2009 | Shelton et al. |
| 2009/0143851 A1 | 6/2009 | Paul, Jr. |
| 2009/0192474 A1 | 7/2009 | Wei et al. |
| 2009/0192609 A1 | 7/2009 | Klabunde et al. |
| 2009/0198197 A1 | 8/2009 | Bischoff et al. |
| 2009/0227948 A1 | 9/2009 | Chen et al. |
| 2009/0233045 A1 | 9/2009 | Slama et al. |
| 2009/0234453 A1 | 9/2009 | Steinberg |
| 2009/0289395 A1 | 11/2009 | Chou |
| 2010/0004729 A1 | 1/2010 | Chew et al. |
| 2010/0028390 A1 | 2/2010 | Cleary et al. |
| 2010/0028402 A1 | 2/2010 | Dobrovolskaia et al. |
| 2010/0070015 A1 | 3/2010 | Schneider et al. |
| 2010/0211153 A1 | 8/2010 | Cook et al. |
| 2010/0222826 A1 | 9/2010 | Bojarski et al. |
| 2010/0228333 A1 | 9/2010 | Drasier et al. |
| 2010/0233238 A1 | 9/2010 | Tenney et al. |
| 2010/0241214 A1 | 9/2010 | Holzer et al. |
| 2010/0247600 A1 | 9/2010 | Xia et al. |
| 2010/0249783 A1 | 9/2010 | Trieu |
| 2011/0144688 A1 | 6/2011 | Reiss et al. |
| 2011/0244047 A1* | 10/2011 | Asari .................. A61K 9/0056 |
| | | | 424/489 |
| 2011/0268781 A1 | 11/2011 | Cleek et al. |
| 2011/0282362 A1 | 11/2011 | Bojarski et al. |
| 2012/0010636 A1 | 1/2012 | Boey et al. |
| 2012/0016388 A1 | 1/2012 | Houard et al. |
| 2012/0027833 A1 | 2/2012 | Zilberman |
| 2013/0129807 A1* | 5/2013 | Devore ................ A61K 47/42 |
| | | | 424/443 |
| 2013/0289621 A1 | 10/2013 | Fulmer et al. |

FOREIGN PATENT DOCUMENTS

| | | |
|---|---|---|
| CN | 1638743 A | 7/2005 |
| CN | 101402736 A | 4/2009 |
| CN | 101437571 | 5/2009 |
| CN | 101912663 A | 12/2010 |
| CN | 102958557 A | 3/2013 |
| DE | 3939363 A1 | 6/1991 |
| EP | 0013638 | 7/1980 |
| EP | 0323800 | 7/1989 |
| EP | 0371819 A2 | 6/1990 |
| EP | 523926 | 1/1993 |
| EP | 0539751 | 5/1993 |
| EP | 0578998 | 1/1994 |
| EP | 604697 | 7/1994 |
| EP | 737703 | 10/1996 |
| EP | 1216717 | 6/2002 |
| EP | 1294323 | 3/2003 |
| EP | 1482996 | 9/2003 |
| EP | 1374817 | 1/2004 |
| EP | 1395303 | 3/2004 |
| EP | 1463463 | 10/2004 |
| EP | 1272131 | 3/2006 |
| EP | 1812090 | 5/2006 |
| EP | 1820463 | 8/2007 |
| EP | 1913903 | 4/2008 |
| EP | 2052700 | 4/2009 |
| EP | 2080603 | 7/2009 |
| FR | 1181333 A | 6/1959 |
| FR | 1183333 | 7/1959 |
| JP | 7-44936 | 4/1988 |
| JP | 02-121652 | 5/1990 |
| JP | 3-85179 | 4/1991 |
| JP | 04-221538 | 8/1992 |
| JP | 07-313586 | 5/1994 |
| JP | 0744936 B2 | 5/1995 |
| JP | 08-024347 | 1/1996 |

(56) References Cited

FOREIGN PATENT DOCUMENTS

| | | |
|---|---|---|
| JP | 09-201330 | 1/1996 |
| JP | 2003-527193 | 3/1996 |
| JP | 08-224297 | 9/1996 |
| JP | 09-173364 | 7/1997 |
| JP | 2011-216178 | 8/1999 |
| JP | 2002-058741 A | 2/2002 |
| JP | 2003-527193 A | 9/2003 |
| JP | 2008-531699 | 8/2008 |
| JP | 2008-224297 A | 9/2008 |
| JP | 2008-535700 | 9/2008 |
| JP | 2009-240783 | 3/2009 |
| JP | 2009-511196 A | 3/2009 |
| JP | 2013-005984 A | 1/2013 |
| RU | 2234419 C2 | 8/2004 |
| RU | 2300792 C2 | 6/2007 |
| RU | 77539 U1 | 10/2008 |
| SU | 683207 A1 | 3/1985 |
| WO | WO 1998/051240 | 11/1998 |
| WO | WO 1999/051171 | 10/1999 |
| WO | WO 1999/062416 | 12/1999 |
| WO | WO 2000/012147 | 3/2000 |
| WO | WO 2001/012107 | 2/2001 |
| WO | WO 2001/32100 A2 | 5/2001 |
| WO | WO 2001/70135 A2 | 9/2001 |
| WO | WO 2001/076514 | 10/2001 |
| WO | WO 2001/097721 | 12/2001 |
| WO | 02/51463 A2 | 7/2002 |
| WO | WO 2003/022165 | 3/2003 |
| WO | WO 2003/059213 | 7/2003 |
| WO | WO 2004/010854 | 2/2004 |
| WO | WO 2005/009499 | 2/2005 |
| WO | 2005/049105 A2 | 6/2005 |
| WO | WO 2006/023261 | 3/2006 |
| WO | WO 2006/050106 | 5/2006 |
| WO | WO 2007/047420 A2 | 4/2007 |
| WO | WO 2007/053022 | 5/2007 |
| WO | WO 2007/092417 | 8/2007 |
| WO | WO 2008/121816 | 10/2008 |
| WO | WO 2010/135440 A1 | 11/2010 |
| WO | 2013/013172 A1 | 1/2013 |

OTHER PUBLICATIONS

Second Office Action for Chinese Application No. 200680037881.8 dated Dec. 23, 2011.

Bailey, "A Meta-Analysis of Extended-Interval Dosing Versus Multiple Daily Dosing of Aminoglycosides", Clinical Infectious Diseases, May 1997, 24, 786-795.

Darouiche, "Treatment of Infections Associated with Surgical Implants", The New England Journal of Medicine, Apr. 2004, 350(14), 1422-1429.

Lucke et al., "Gentamicin Coating of Metallic Implants Reduces Implant-Related Osteomyelitis in Rats", Bone, May 2003, 32, 521-531.

Mingeot-Leclercq et al., "Aminoglycosides: Nephrotoxicity", Antimicrobial Agents and Chemotherapy, May 1999, 43(5), 1003-1012.

Pineros-Fernandez et al.,"CAPROSYN, Another Major Advance in Synthetic Monofilament Absorbable Suture", Journal of Long-Term Effects of Medical Implants, 2004, 14(5), 359-368.

Trampuz et al., "Diagnosis and Treatment of Infections Associated with Fracture-Fixation Devices", Injury, May 2006, 37, Suppl 2, S59-S66.

Final Office Action for Japanese Patent Application No. 2008-535700 dated May 24, 2012.

Office Action dated Oct. 18, 2011 for Japanese Patent Application No. 2008-535700.

International Search Report for Application No. PCT/US2006/40038, dated Sep. 25, 2007, 5 pages.

Written Opinion of the International Searching Authority for Application No. PCT/US2006/40038, dated Sep. 25, 2007, 6 pages.

European Patent Application o. 04750971.6, Communication dated Jun. 12, 2008, 5 pages.

International Application Serial No. PCT/US06/40038, International Preliminary Report on Patentability dated Sep. 3, 2008, 7 pages.

Kaneko et al., "Synthesis and Swelling—deswelling kinetics of poly(N-isopropylacrylamide) hydrogels grafted with LCST modulated polymers", Journal of Biomaterials Science, Polymer Edition, 10(11), 1079-1091, 1999.

Stile et al., "Synthesis and Characterization of Injectable Poly(N-isopropylacrylamide)-Based Hydrogels That Support Tissue Formation in Vitro", Macromolecules, 32, (1999), 7370-7379.

Japanese Application No. 2002-506661, Notice of the Reason for the Rejection dated Feb. 27, 2008, (w/ English Translation) 7 pages.

Japanese Application No. 2002-506661, Official Notice of Reason for the Final Rejection dated Jul. 11, 2008, (w/ English Translation), 4 pages.

Aviv et al., "Gentamicin-Loaded Bioresorbable Films for Prevention of Bacterial Infections Associated with Orthopedic Implants", Journal of Biomedical Materials Research Part 1, Mar. 2007, 10 pages.

Gosau et al., "Release of Gentamicin Sulphate From Biodegradable PLGA-Implants Produced by Hot Melt Extrusion", Pharmazie, 2010, 6 pages.

International Patent Application No. PCT/US2012/071708: International Search Report and Written Opinion dated Jun. 5, 2013, 22 pages.

Machine Translation of DE 3939363 A1, Jun. 1991, 9 pages.

Von Plocki et al., "Biodegradable Sleeves for Metal Implants to Prevent Implant-Associated Infection: An Experimental In Vivo Study in Sheep", Vet Surg., Apr. 2012, 41(3), 410-421, Epub Jan. 12, 2012.

Zhang et al., Biodegradable Controlled Antibiotic Release Devices for Osteomyelitis: Optimization of Release Properties, Journal of Pharmacy and Pharmacology, Sep. 1994, vol. 46, Issue 9.

Pandey et al., Characterization of In-vitro Release of Gentamicin from Biodegradable Polymer Thin Films Microstructure-Function Relationship by Confocal Raman Microscopy, Apr. 2015, Journal of Biomedical Materials Research.

Fredenberg et al., The mechanisms of drug release in polyl(lactic-co-glycolic acid)-based delivery systems—A review, Aug. 2011, International Journal of Pharmaceutics, vol. 415, Issues 1-2, pp. 34-52.

Huang et al., On the Importance and mechanisms of burst release in matrix-controlled drug delivery systems, Jun. 2001, Journal of Controlled Release, vol. 73, Issues 2-3, pp. 121-136.

Schmidt et al., Antibiotic in vivo/in vitro release, histocompatibility and biodegradation of gentamicin implants based on lactic acid polymers and copolymers, Nov. 1995, Journal of Controlled Release, vol. 37, Issues 1-2, pp. 83-84.

Dorta et al., Potential applications of PLGA film-implants in modulating in vitro drugs release, Nov. 2002, International Journal of Pharmaceutics, vol. 248, Issues 1-2, pp. 149-156.

Gupta et al., Cefoperazone sodium impregnated polycaprolactone composite implant for osteomyelitis, Indian J. Pharm Sci, Jul.-Aug. 2009, 71(4) 377-381.

Louis et al., "Resorbable Mesh as a Containment System in Reconstruction of the Atrophic Mandible Fracture", J Oral Maxillofac Surg, 62, pp. 719-723, Jun. 2004.

* cited by examiner

FILMS AND METHODS OF MANUFACTURE

CROSS-REFERENCE TO RELATED APPLICATIONS

This application claims the benefit of U.S. Provisional Patent Application No. 61/580,679 filed Dec. 28, 2011 entitled "Films and Methods of Manufacture", which is hereby incorporated by reference in its entirety.

BACKGROUND OF THE INVENTION

The present invention generally relates to films (e.g., polymer films) and methods of manufacture, and in at least some embodiments, perforated films and methods of manufacture for medical use.

BRIEF SUMMARY OF THE INVENTION

In one embodiment there is a flexible body comprising a film (e.g., a polymer film) having a first surface and an opposing second surface, the film having a plurality of apertures extending from the first surface to the second surface and a plurality of raised lips protruding from the first surface such that each of the plurality of apertures is surrounded by a one of the plurality of raised lips. In a preferred embodiment, the film is comprised of a polymeric material (i.e., a polymer film). In one embodiment, the polymer film comprises a bioresorbable polymer. In one embodiment, the bioresorbable polymer contains repeat units selected from the group consisting of: L-lactic acid, D-lactic acid, L-lactide, D-lactide, D,L-lactide, glycolide, a lactone, a lactam, trimethylene carbonate, a cyclic carbonate, a cyclic ether, para-dioxanone, beta-hydroxybutyric acid, beta-hydroxypropionic acid, beta-hydroxyvaleric acid, and a combination thereof. In one embodiment, the bioresorbable polymer contains repeat units selected from the group consisting of: L-lactic acid, D-lactic acid, L-lactide, D-lactide, D,L-lactide, ε-caprolactone, trimethylene carbonate, para-dioxanone, and a combination thereof. In one embodiment, the bioresorbable polymer is a copolymer of glycolide, trimethylene carbonate, lactide and caprolactone.

In one embodiment, the first surface includes a contiguous planar portion extending between the plurality of raised protruding lips. In one embodiment, the plurality of raised protruding lips each have an outer edge that is raised above the contiguous planar portion by approximately 0.1 mm to approximately 1.0 mm. In one embodiment, the polymer film comprises a plurality of discrete eluting drug components and wherein the polymer film is configured to elute the plurality of discrete drug components at different time periods following implantation of the flexible body. In a further embodiment, the flexible body comprises at least one seam configured to form the polymer film into a sheath. In one embodiment, the polymer film has a first tensile strength in a first planar direction and a second tensile strength in a second planar direction that is perpendicular to the first planar direction, wherein the first tensile strength is substantially equal to the second tensile strength. In one embodiment, the polymer film has a nominal thickness of no greater than 0.06 mm. In one embodiment, the first surface has a first tactile feel that is different from a second tactile feel of the second surface.

In another embodiment there is a method of producing a polymer film comprising: placing a polymer solution into a one sided mold having a plurality of protrusions extending from a bottom of the mold wherein the polymer solution is characterized by a viscosity that inhibits the unaided flow of the polymer throughout the mold; urging the polymer solution around each of the plurality of protrusions; and solidifying the polymer solution. In one embodiment, the mold includes a perimeter form extending to an elevation that is substantially equal to an elevation of each of the plurality of protrusions. In one embodiment, the urging comprises drawing an urging means such as a blade, bar, squeegee or roller across the perimeter form and the plurality of protrusions to force the polymer solution to flow around the plurality of protrusions and throughout the mold such that the polymer solution has a substantially uniform thickness. In one embodiment, an outer surface of each of the protrusions is substantially free of polymer solution after the drawing. In one embodiment, the placing step includes depositing the polymer solution in the mold such that a portion of the polymer solution is above the elevation of the perimeter form and the protrusions.

In one embodiment, solidifying the polymer solution includes reducing a thickness of the polymer solution. In one embodiment, solidifying the polymer solution includes forming a meniscus of solidified polymer around each of the plurality of protrusions. In one embodiment, a distance from the bottom of the mold to a top of each of the plurality of protrusions is less than approximately 0.3 mm. In one embodiment, the polymer solution contains a drug. In one embodiment, the polymer solution is formed by combining a solvent, a polymer, and the drug at a temperature below 90° C. In one embodiment, the perimeter form defines a total mold area and the plurality of protrusions define an area that is at least about 15% of the total mold area. In a further embodiment, the method comprises peeling the drug eluting film from the mold.

In one embodiment, the polymer solution comprises a cross-linkable pre-polymer solution. In one embodiment, the solidifying step includes cross-linking the polymer by applying UV radiation, temperature change, polymerization catalysts, soluble crosslinking agents or combinations thereof to the polymer solution. In one embodiment, the polymer solution includes discrete drug units. In one embodiment, the polymer solution comprises a first solvent and a polymer and the solidifying step includes exposing the polymer solution to a second solvent in which the first solvent is soluble and in which the polymer and the drug are not soluble such that the first solvent is at least substantially removed from the polymer solution and the polymer solidifies to contain the drug.

BRIEF DESCRIPTION OF THE SEVERAL VIEWS OF THE DRAWINGS

The foregoing summary, as well as the following detailed description of embodiments of the polymer films and methods of manufacture, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Infections represent a major challenge in orthopedic or trauma surgery. Despite prophylactic measures like asepsis and antisepsis, the surgery site is still a site of access for local pathogens to become virulent and cause infections.

Coating an implantable device with a drug such as an antibiotic, has been effective to reduce infection. However, given the large number, sizes, and shapes of implants and other medical devices, the regulatory, financial, and logistical burden of providing a coating for each device is enormous. The problem is amplified if one considers additional drugs to use in coatings such as analgesics, antineoplastic agents and growth promoting substances.

Embodiments of the present invention are directed to improved perforated polymer films and novel casting methods of making the same. In some embodiments, the films are for use with implantable medical devices though the films may be used in any application.

Commercial methods of forming a perforated film currently existing generally involve forming a solid film as a first step, then punching or cutting holes into the film as a second step. An advantage of at least some of the embodiments described herein is that the holes or perforations of the film are formed at the same time that the film is formed. This may be useful when the polymer film formed is very thin and at risk for damage due to subsequent handling or processing or when the thickness and/or strength of the film makes it difficult to punch or cut by traditional methods without damaging the film. Such a process may also be advantageous when the polymer solution contains a drug or other active that may be damaged by subsequent cutting or punching steps.

Embodiments of the present invention may also be useful for making quantities of cast film such as those which are considered too small to make economically by traditional methods which are typically continuous processes designed for high volume production. An additional advantage of at least some embodiments of the invention is that perforations formed in the cast sheet can have complex shapes. A further advantage of at least some of the embodiments of the invention is that at least one side of the film may be formed to have a non-planar surface which in some embodiments increases friction and gives an improved tactile feel. These advantages of the present invention, as well as others, are described in further detail below.

Figure 1A:
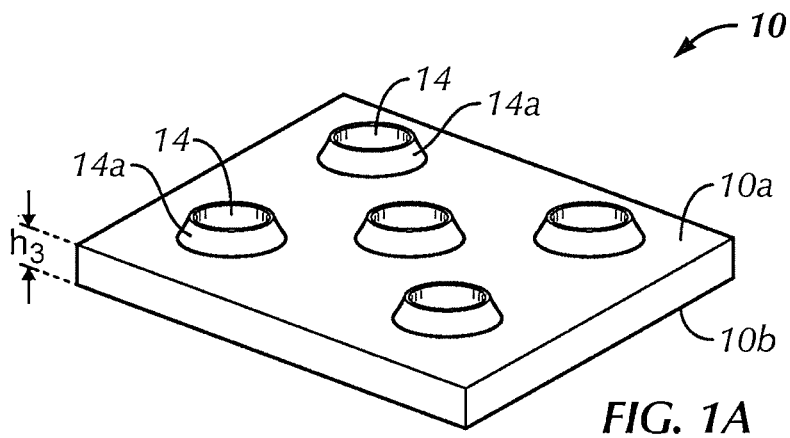
FIG. 1A is an enlarged perspective schematic view of a portion of a film (in this instance a polymer film) in accordance with an exemplary embodiment of the present invention.
Figure 1B:
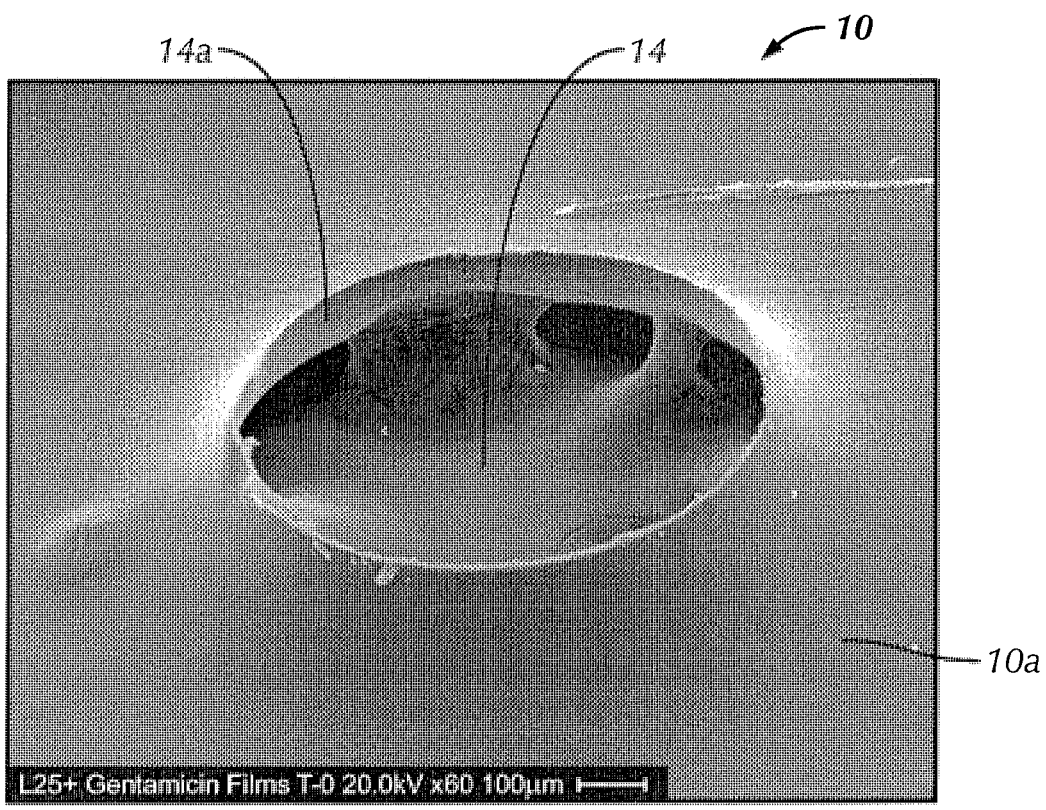
FIG. 1B is a 60× magnified photo of an aperture of a polymer film in accordance with an exemplary embodiment of the present invention.

Referring to the drawings in detail, wherein like reference numerals indicate like elements throughout, there is shown in FIGS. 1A and 1B polymer films, generally designated 10, and molds, generally designated 18, in accordance with exemplary embodiments of the present invention.

Referring to the embodiment of FIG. 1A, film 10 (e.g., a polymer film) is a flexible body having a first surface 10a and an opposing second surface 10b.

Figure 2:
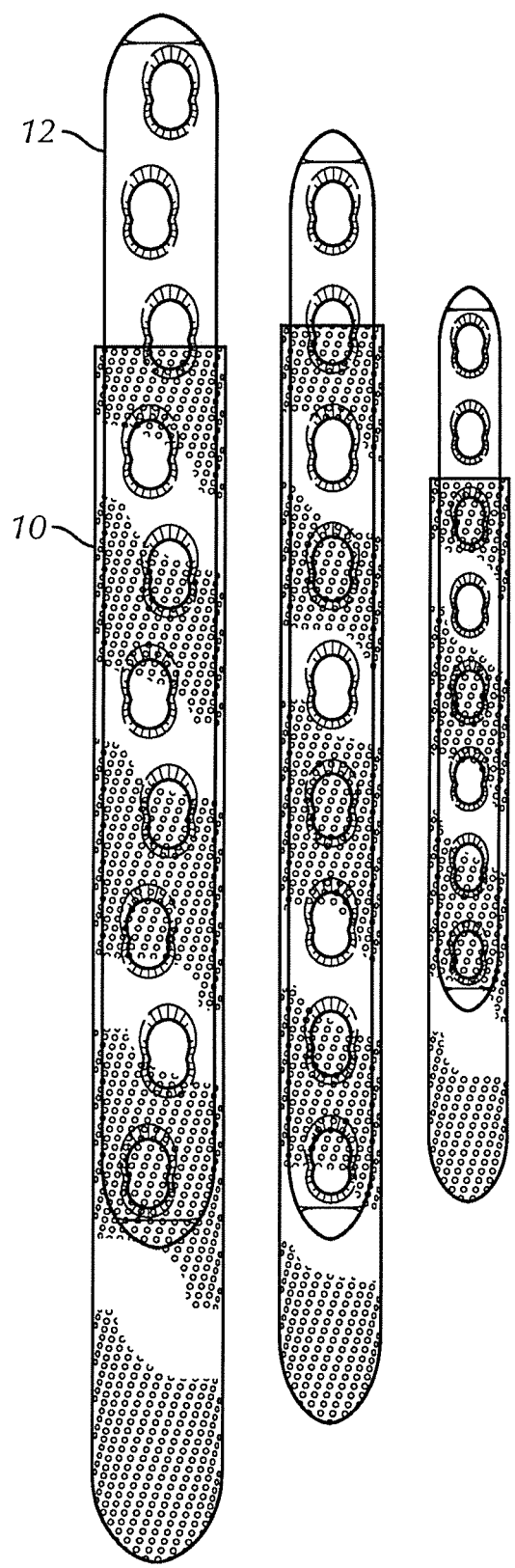
FIG. 2 is a top view of three exemplary sheaths formed from the polymer film of FIG. 1B in combination with a respective implantable medical device.
Figure 3A:
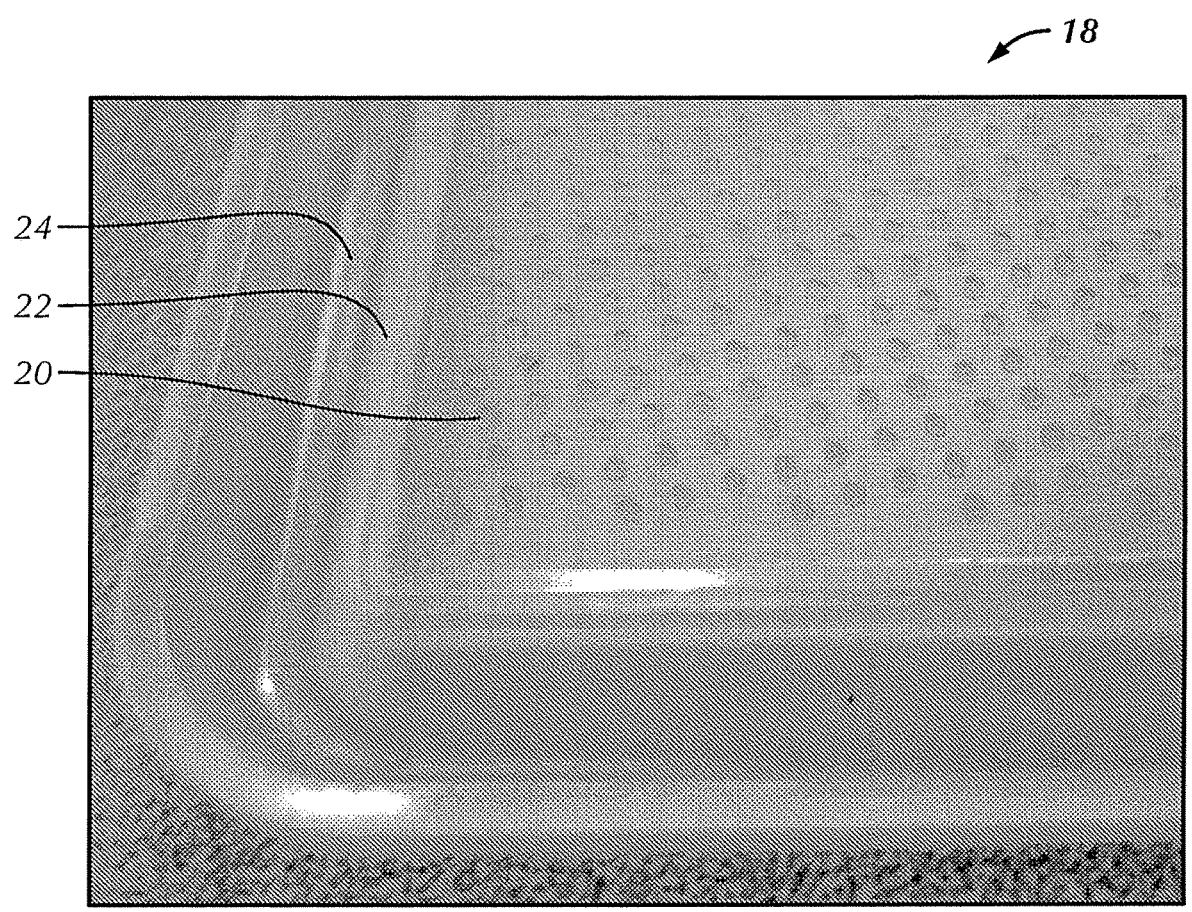
FIG. 3A is a perspective photograph of a portion of a mold in accordance with an exemplary embodiment of the present invention.
Figure 3B:
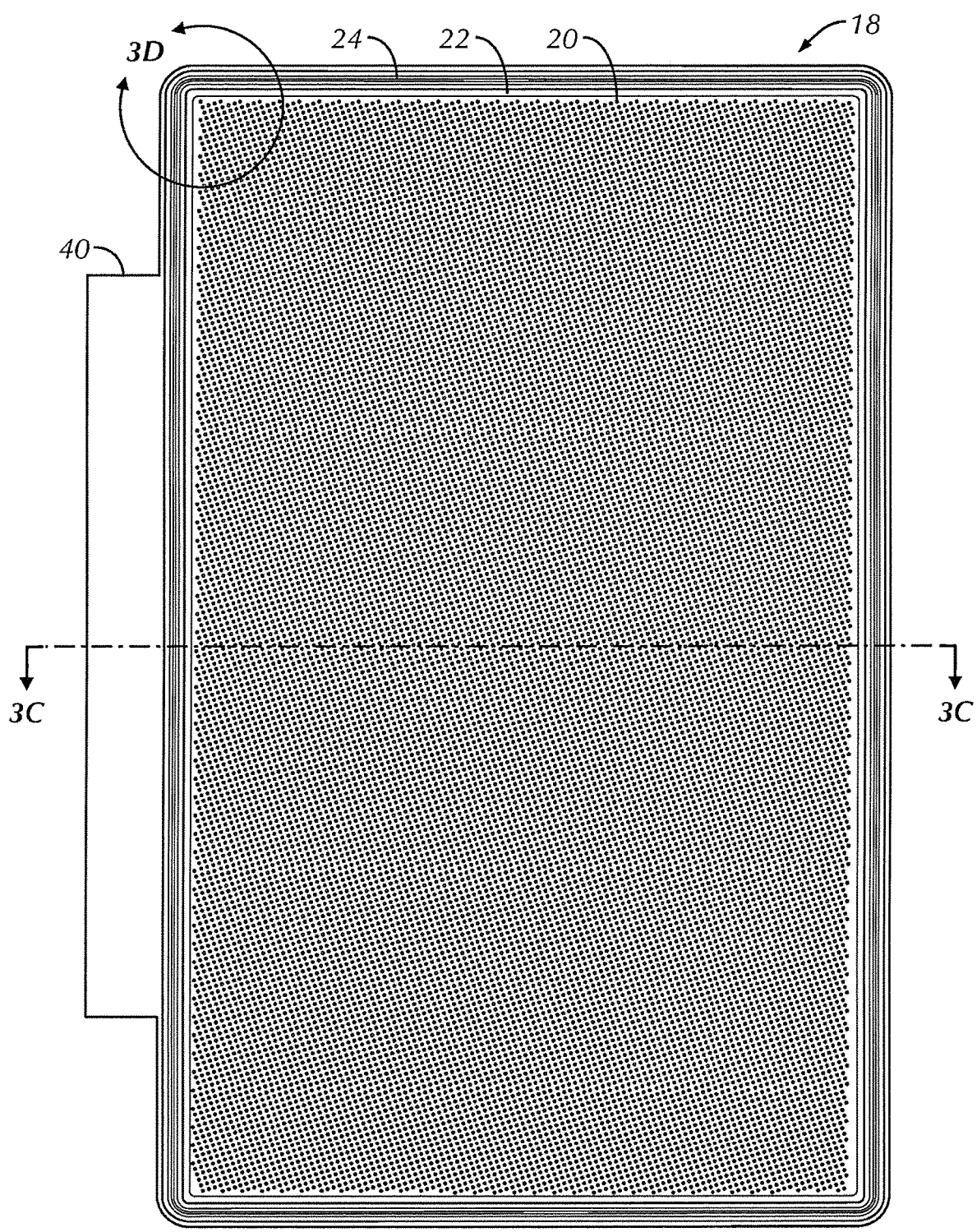
FIG. 3B is a top plan view of the mold of FIG. 3A.
Figure 3C:
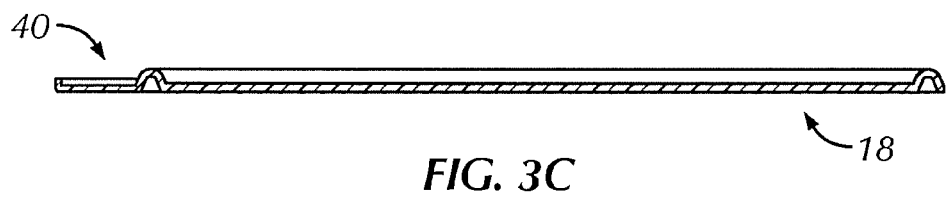
FIG. 3C is a cross-sectional side view of the mold of FIG. 3B taken about line C-C in FIG. 3B.
Figure 3D:
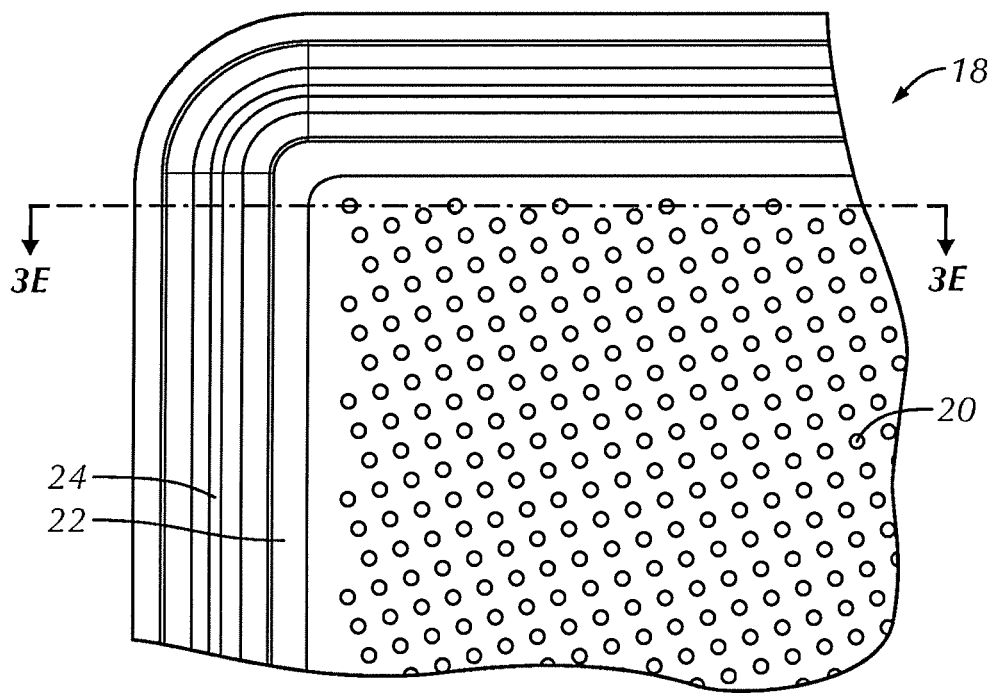
FIG. 3D is an enlarged corner section of the mold shown in FIG. 3B.
Figure 3E:
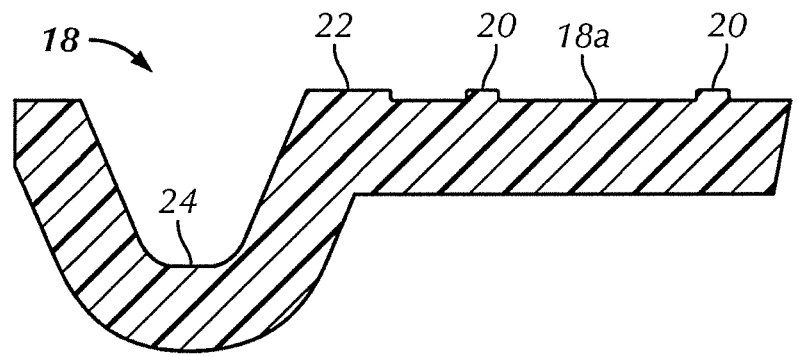
FIG. 3E is an enlarged cross section of the mold shown in FIG. 3D taken along line B-B.
Figure 3F:
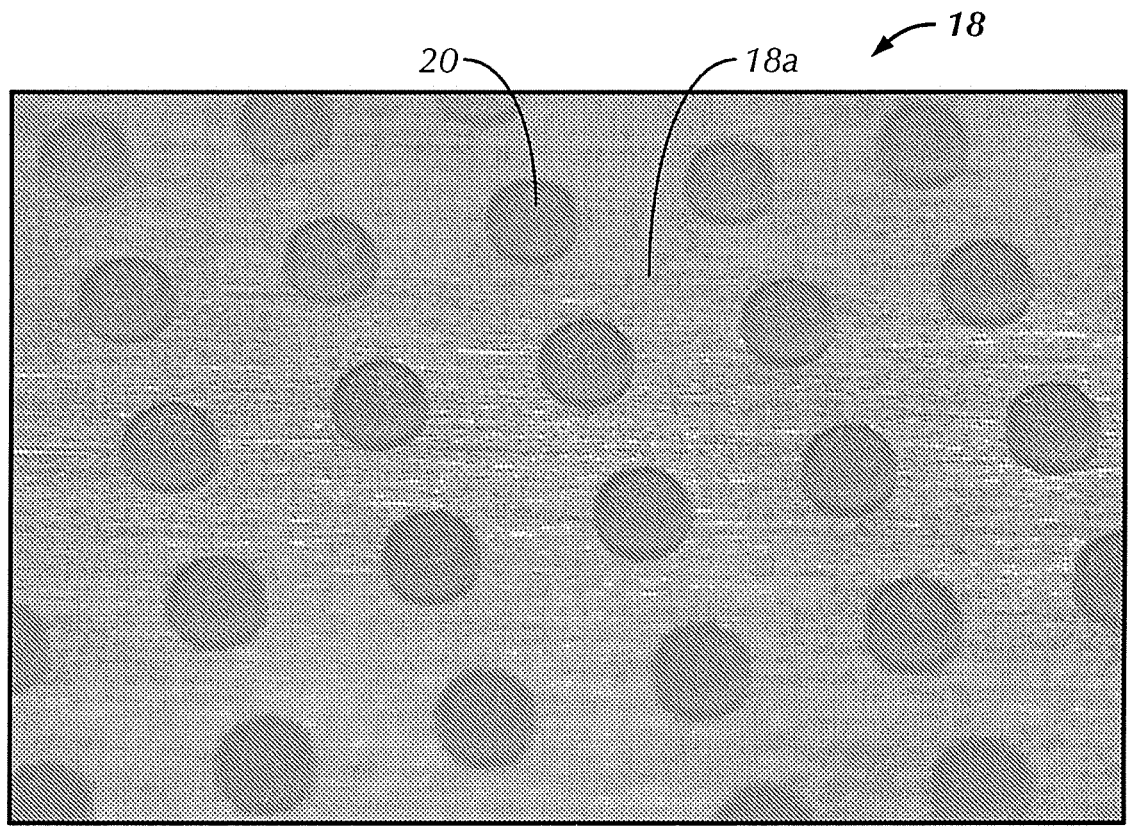
FIG. 3F is an enlarged perspective photograph of the mold of FIG. 3A.
Figure 3G:
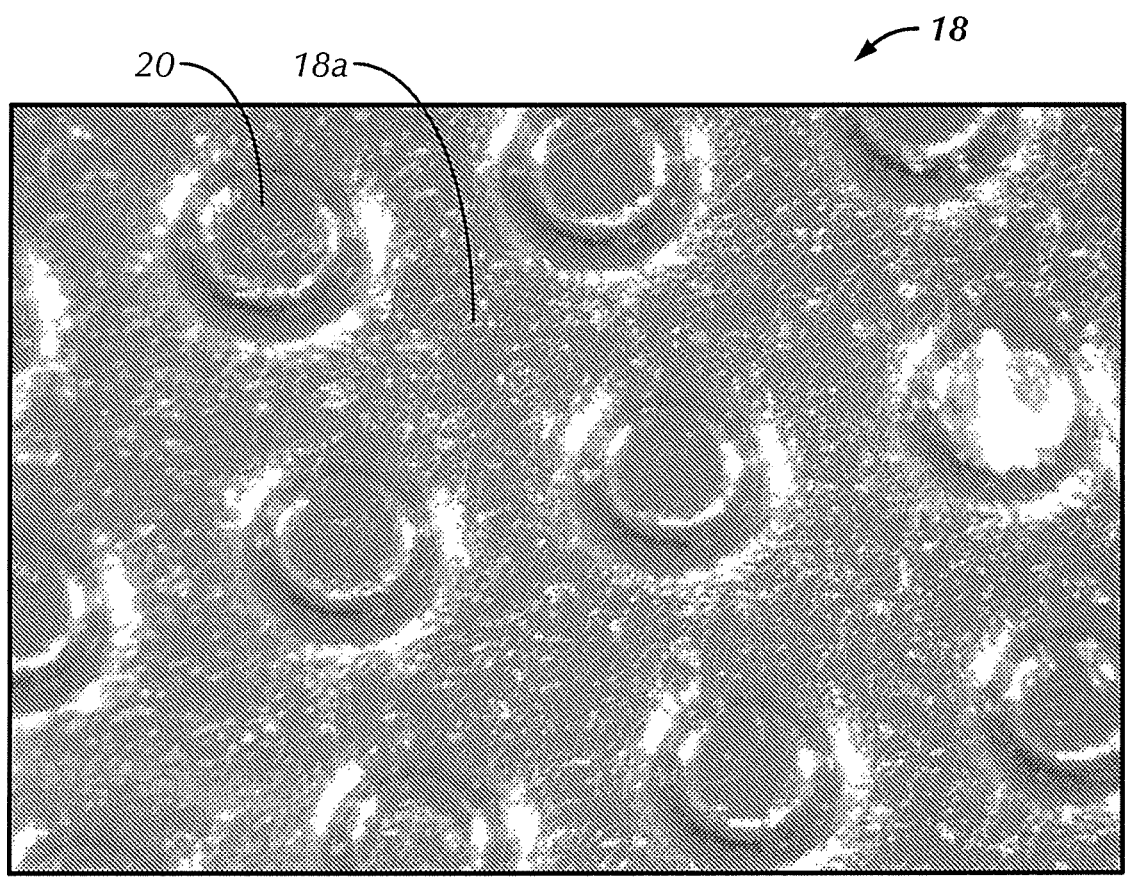
FIG. 3G is an enlarged perspective photograph of a mold in accordance with another exemplary embodiment of the present invention.

In one embodiment, film 10 may be formed from a single thin sheet of a biologically-compatible material. In one embodiment, film 10 is comprised of two or more sheets of material. In a preferred embodiment, the biologically-compatible material is bioresorbable. In embodiments used with a medical (see FIG. 2), film 10, in some embodiments, will dissolve away over time when implanted in vive and be absorbed into a patient, leaving only medical device 12 behind (such as if medical device 12 is not also made of a bioresorbable material). Medical device 12 may also be made of a bioresorbable material in other embodiments in which case both medical device 12 and film 10 will eventually dissolve. In some embodiments, film 10 may be configured to absorb at a different rate from an absorbable medical device 12 (e.g., a faster or a slower rate).

In some embodiments, a bioresorbable film 10 has advantages over non-resorbable meshes which, for example, can become encased with or embedded in dense fibrous tissue or present other issues associated with long term foreign body exposure. In some embodiments, film 10 is only partially bioresorbable.

A bioabsorbable polymer may be used in order to provide a controlled release of a drug such as an antibiotic, with a definite end point. Continuous, long term presence of an antibiotic is often undesirable, since this can create conditions for development of antibiotic resistant bacteria. In one embodiment, complete degradation of film 10 ensures that the drug will be completely released in a pre-determined and/or selectable time. In one embodiment, the drug release can be completely released or substantially completely released even where the film 10 is not fully absorbed.

The absorption of film 10 may also impact and/or control the release of the antibiotic in the continuous release phase. As the film degrades, for example, the permeability of the film may increase, and more drug may be released. In some embodiments, the polymer used must be for a structure that is flexible, have relatively high tensile strength, and be able to be processed by solution casting. In one embodiment, film 10 is comprised of a co-polymer that includes one or more of four monomers; glycolide, lactide, caprolactone, and trimethylene carbonate. Glycolide may be included and may have the effect of speeding up degradation of film 10. Lactide may also be included and may have the effect of increasing mechanical strength of film 10. Caprolactone and trimethylene carbonate may be used and may have the effect of increasing flexibility of film 10.

In one embodiment, the bioresorbable polymer includes one or more of PLA, PGA, polycaprolactone, polydioxanone, TMC and copolymers of these. In one embodiment, the bioresorbable polymer is produced from a copolymer of glycolic acid, caprolactone lactic acid, and trimethylene carbonate. In one embodiment, the bioresorbable polymer is produced from a copolymer of approximately 60% glycolic acid, approximately 20% caprolatone, approximately 10% lactic acid and approximately 10% trimethylene carbonate. In one embodiment, the bioresorbable polymer contains repeat units selected from the group consisting of: L-lactic acid, D-lactic acid, L-lactide, D-lactide, D,L-lactide, glycolide, a lactone, a lactam, trimethylene carbonate, a cyclic carbonate, a cyclic ether, para-dioxanone, beta-hydroxybutyric acid, beta-hydroxypropionic acid, beta-hydroxyvaleric acid, and a combination thereof. In one embodiment, the bioresorbable polymer contains repeat units selected from the group consisting of: L-lactic acid, D-lactic acid, L-lactide; D-lactide, D,L-lactide, ε-caprolactone, trimethylene carbonate, para-dioxanone, and a combination thereof. In one embodiment, the bioresorbable polymer is a copolymer of glycolide, trimethylene carbonate, lactide and caprolactone. Film 10 may also or alternatively include natural biopolymers such as alginate, chitosan, collagen, gelatin, hyaluronate, zein and others.

Still referring to FIG. 1A, film 10 may be configured to have any preferred dimensions including thickness $h_3$ measured between first surface 10a and second surface 10b not inclusive of the raised lips 14a that are illustrated in FIGS. 1A and 1B as surrounding apertures 14. In one embodiment, film 10 must be thin enough such that it does not interfere with the mechanical interlocking between a plate 12 and the screws used in fixation (such as where if the film is trapped between the plate and screw). In some embodiments, thickness $h_3$ is minimized as much as possible. In one embodiment, the thickness of film 10 is selected such that degradation of film 10 does not cause significant loosening of a connection to medical device 12 such as a plate-screw construct.

In some embodiments, thickness $h_3$ of film 10 is approximately 0.05 mm. In some embodiments, thickness $h_3$ of film 10 is approximately no greater than 0.05 mm. In some embodiments, thickness $h_3$ of film 10 is less than approximately 0.05 mm. In some embodiments, thickness $h_3$ of film 10 is approximately 0.06 mm. In some embodiments, thickness $h_3$ of film 10 is approximately 0.07 mm. In some embodiments, thickness $h_3$ of film 10 is approximately 0.08 mm. In some embodiments, thickness $h_3$ of film 10 is approximately 0.09 mm. In some embodiments, thickness $h_3$ of film 10 is approximately 0.1 mm. In some embodiments, thickness $h_3$ of film 10 is approximately 0.2 mm. In some embodiments, thickness $h_3$ of film 10 is approximately 0.3 mm. In some embodiments, thickness $h_3$ of film 10 is approximately 0.4 mm. In some embodiments, thickness $h_3$ of film 10 is approximately 0.5 mm.

In one embodiment, thickness $h_3$ of film 10 is approximately uniform throughout film 10. In some embodiments, film 10 is tapered toward on or more edges along the outer periphery. In some embodiments, thickness $h_3$ of film 10 differs in two or more sections to control strength or drug delivery of each area.

In some embodiments, film 10 must be of sufficient strength to withstand mechanical forces such as implantation, drilling and screw placement. In one embodiment, film 10 has a first tensile strength in a first planar direction and a second tensile strength in a second planar direction that is perpendicular to the first planar direction, where the first tensile strength is substantially equal to the second tensile strength. In one embodiment, film 10 has the strength characteristics as listed in tables 1-3 below.

TABLE 1

| Film Sample | Start Date | Specimen label | Length (mm) | Width (mm) | Thickness (mm) | Tensile strain at Yield (Offset 0.2%) (%) |
|---|---|---|---|---|---|---|
| 1 | Jun. 2, 2009 9:02 AM | Day 0 Sample 1 | 50.00 | 10.510 | 0.059 | 2.44051 |
| 2 | Jun. 2, 2009 9:05 AM | Day 0 Sample 2 | 50.00 | 11.160 | 0.063 | 3.43452 |
| 3 | Jun. 2, 2009 9:07 AM | Day 0 Sample 3 | 50.00 | 11.230 | 0.062 | 2.04468 |
| 4 | Jun. 2, 2009 9:09 AM | Day 0 Sample 4 | 50.00 | 10.740 | 0.057 | 2.81023 |

TABLE 1-continued

| Film Sample | Start Date | Specimen label | Length (mm) | Width (mm) | Thickness (mm) | Tensile strain at Yield (Offset 0.2%) (%) |
|---|---|---|---|---|---|---|
| 5 | Jun. 2, 2009 9:13 AM | Day 0 Sample 5 | 50.00 | 11.180 | 0.066 | 3.06678 |
| 6 | Jun. 2, 2009 9:15 AM | Day 0 Sample 6 | 50.00 | 10.920 | 0.058 | 3.65944 |
| Mean | | | 50.00 | 10.957 | 0.061 | 2.90936 |
| Standard Deviation | | | 0.000 | 0.288 | 0.003 | 0.607 |
| Coefficient of Variation | | | 0.000 | 2.625 | 5.639 | 20.854 |

TABLE 2

| Film Sample | Tensile stress at Yield (Offset 0.2%) (MPa) | Tensile strain at Maximum Load (%) | Tensile stress at Maximum Load (MPa) | Tensile strain at Break (Standard) (%) |
|---|---|---|---|---|
| 1 | 13.75364 | 22.50031 | 26.31165 | 31.66499 |
| 2 | 14.00508 | 31.66468 | 27.57964 | 49.99874 |
| 3 | 9.25147 | 32.49843 | 26.60082 | 149.99967 |
| 4 | 12.82553 | 26.66562 | 28.46340 | 55.83280 |
| 5 | 13.53060 | 23.33406 | 26.59371 | 36.66562 |
| 6 | 12.60631 | 35.83187 | 26.79990 | 212.49840 |
| Mean | 12.66211 | 28.74916 | 27.05819 | 89.44337 |
| Standard Deviation | 1.756 | 5.393 | 0.812 | 74.322 |
| Coefficient of Variation | 13.865 | 18.760 | 3.000 | 83.094 |

TABLE 3

| Film Sample | Tensile stress at Break (Standard) (MPa) | Modulus (Automatic Young's) (MPa) |
|---|---|---|
| 1 | 15.20147 | 749.15765 |
| 2 | 21.71590 | 504.50877 |
| 3 | 19.08817 | 657.83084 |
| 4 | 18.08469 | 574.31825 |
| 5 | 18.71550 | 618.69300 |
| 6 | 21.75346 | 436.82724 |
| Mean | 19.09320 | 590.22262 |
| Standard Deviation | 2.460 | 111.150 |
| Coefficient of Variation | 12.885 | 18.832 |

In one embodiment, film 10 has a tensile strain at yield (Offset 0.2%) of approximately 2% to approximately 4% and/or a mean tensile strain of approximately 3%. In one embodiment, film 10 has a tensile stress at yield (Offset 0.2%) of approximately 9 MPa to approximately 14 MPa, and/or a mean tensile stress at yield of approximately 12.5 MPa. In one embodiment, film 10 has a tensile stress at maximum load of approximately 25 MPa to approximately 30 MPa, and/or a mean tensile stress at maximum load of approximately 27 MPa. In one embodiment, film 10 has a tensile strain at break (standard) of approximately 30% to approximately 215%, and/or a mean tensile strain at break of approximately 89%. In one embodiment, film 10 has an automatic Young's modulus of approximately 430 MPa to approximately 750 MPa, and/or a mean automatic Young's modulus of approximately 590 MPa. Film 10 may be characterized by combination of one or more of the foregoing properties.

Referring to FIGS. 1A, 1B, 2 and 11E, in some embodiments, film 10 includes a plurality of perforations or apertures 14. In one embodiment, apertures 14 allow the passage or transport of fluids through film 10 (e.g., when implanted near living tissue). In some embodiments, it may be important to allow for fluid flow from one side of the sleeve to the other (inside to outside) in order, for example, to avoid creating a "dead space" between film 10 and medical device 12. Additionally, perforations 14 may advantageously provide more even distribution of the drug or biological agent to adjacent tissue and bone as the material leaches out of the polymer than a sleeve without such perforations.

Apertures 14 may be configured to be any size and shape. In one embodiment, apertures 14 are defined by substantially cylindrical sidewalls. In some embodiments, apertures 14 have sidewalls that have segments that are inwardly facing convex surfaces. In some embodiments, the inwardly facing convex surface is substantially parabolic. Apertures 14 need not be perfectly round in cross section, and in some embodiments, may be ovoid, elliptical, star or diamond in shape. In some embodiments, apertures 14 extend to one or more apexes. In one embodiment, such apexes promote tears in film 10 during use (e.g., where a zone of weakness is created by the aperture). In one embodiment, apertures 14 extend completely through sheet 12 from an inside surface 10b to an outside surface 10a (see FIG. 4C). In one embodiment, one or more apertures 14 extend only partially through film 10 to control drug release or increase the initial strength of film 10.

Apertures 14 may be configured to allow for any desired porosity of film 10. In one embodiment, the porosity of film 10 is greater than approximately 0.01. In one embodiment, the porosity of film 10 is greater than approximately 0.02. In one embodiment, the porosity of film 10 is greater than approximately 0.03. In one embodiment, the porosity of film 10 is greater than approximately 0.04. In one embodiment, the porosity of film 10 is greater than approximately 0.05. In one embodiment, the porosity of film 10 is greater than approximately 0.06. In one embodiment, the porosity of film 10 is greater than approximately 0.07. In one embodiment, the porosity of film 10 is greater than approximately 0.08. In one embodiment, the porosity of film 10 is greater than approximately 0.09. In one embodiment, the porosity of film 10 is greater than approximately 0.10. In one embodiment, the porosity of film 10 is greater than approximately 0.11. In one embodiment, the porosity of film 10 is greater than approximately 0.12. In one embodiment, the porosity of film 10 is greater than approximately 0.13. In one embodiment, the porosity of film 10 is greater than approximately 0.15. In one embodiment, the porosity of film 10 is greater than approximately 0.15. In one embodiment, the porosity of film 10 is greater than approximately 0.16. In one embodiment, the porosity of film 10 is greater than approximately 0.17. In one embodiment, the porosity of film 10 is greater than approximately 0.18. In one embodiment, the porosity of film 10 is greater than approximately 0.19. In one embodiment, the porosity of film 10 is greater than approximately 0.20.

Figure 11A:
FIG. 11A is a top plan view of a sheath formed using the polymer film of FIG. 1 shown in a first configuration.
Figure 11B:
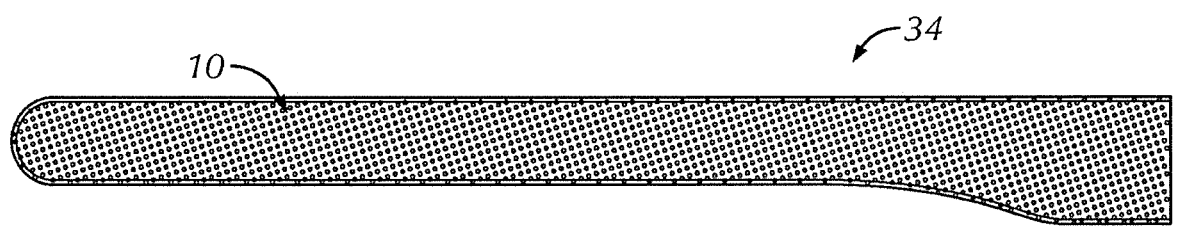
FIG. 11B is a top plan view of a sheath formed using the polymer film of FIG. 1 shown in a second configuration.
Figure 11C:
FIG. 11C is a top plan view of a sheath formed using the polymer film of FIG. 1 shown in a third configuration.
Figure 11D:
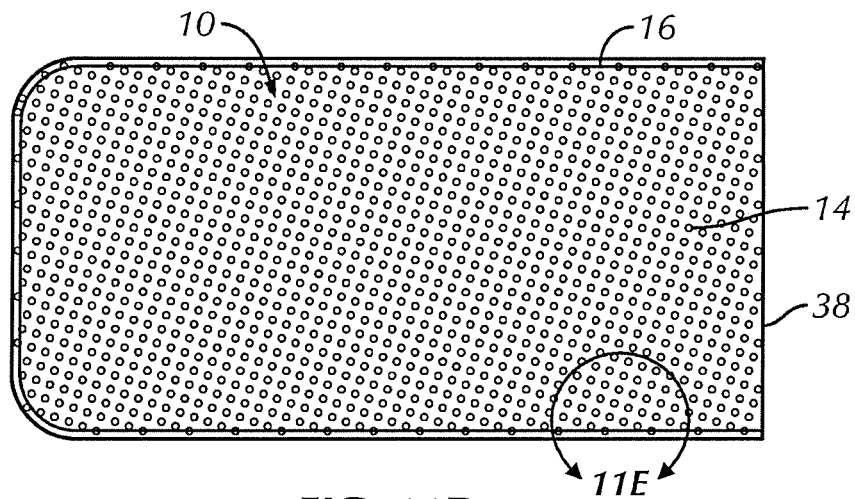
FIG. 11D is a top plan view of a sheath formed using the polymer film of FIG. 1 shown in a fourth configuration.
Figure 11E:
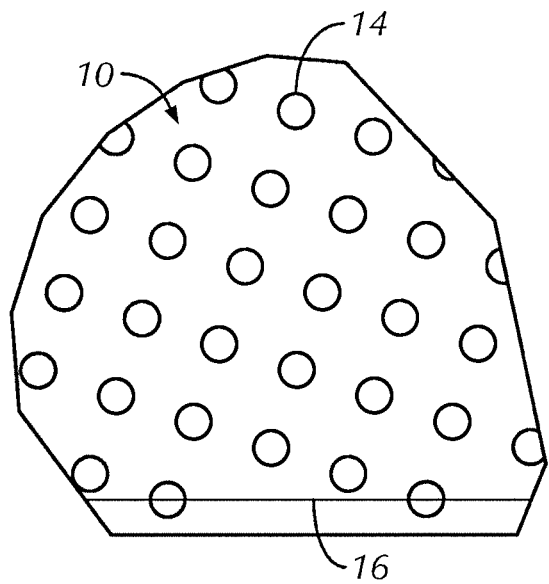
FIG. 11E is the area within circle B in FIG. 11D.
Figure 11F:
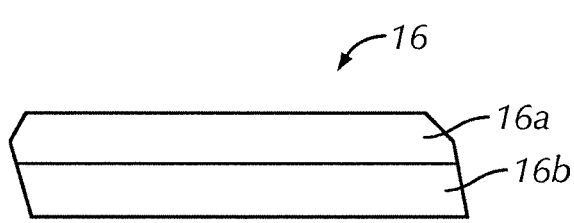
FIG. 11F is an enlarged view of a seam of a sheath such as those shown in FIGS. 11A-11D.
Figure 12:
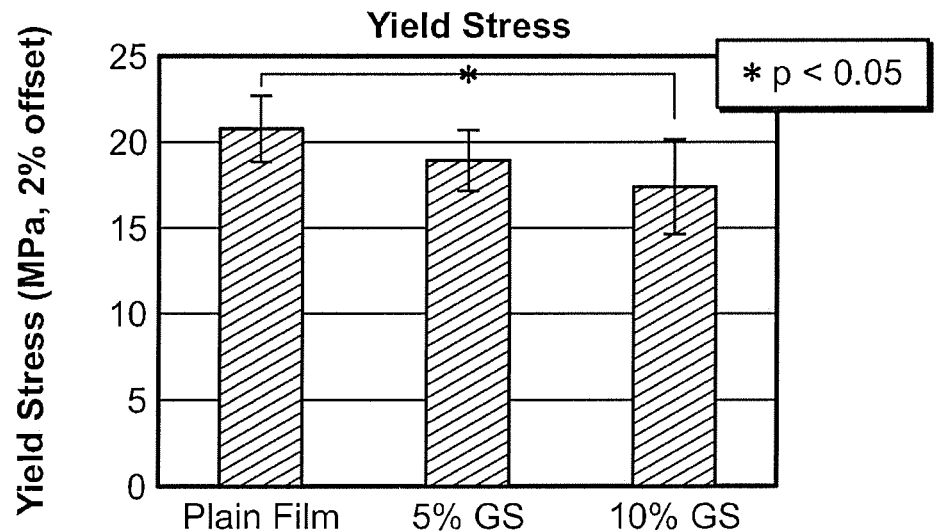
FIG. 12 is a yield stress graph of a polymer film in accordance with an exemplary embodiment of the present invention.
Figure 13:
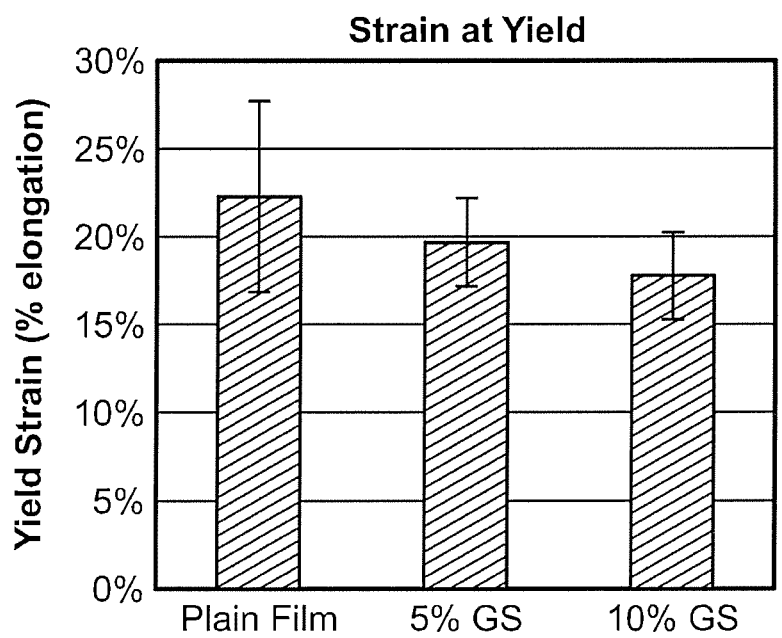
FIG. 13 is a strain at yield graph of a polymer film in accordance with an exemplary embodiment of the present invention.
Figure 14:
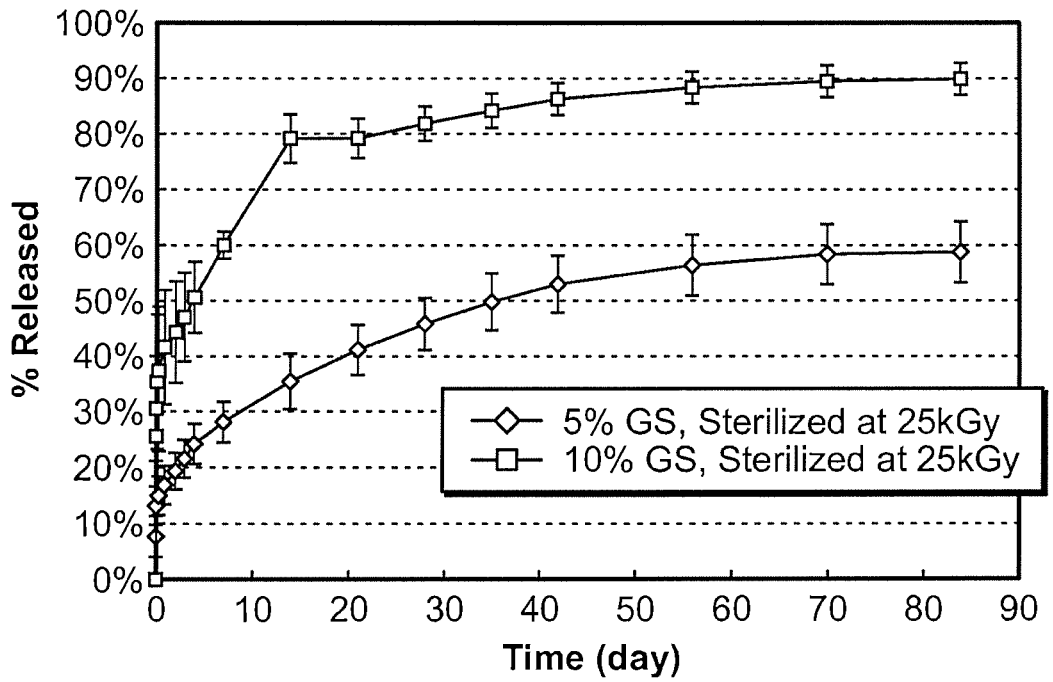
FIG. 14 is a graph illustrating the rate of drug release over time when a sleeve in accordance with an exemplary embodiment of the present invention is placed into saline solution.
Figure 15:
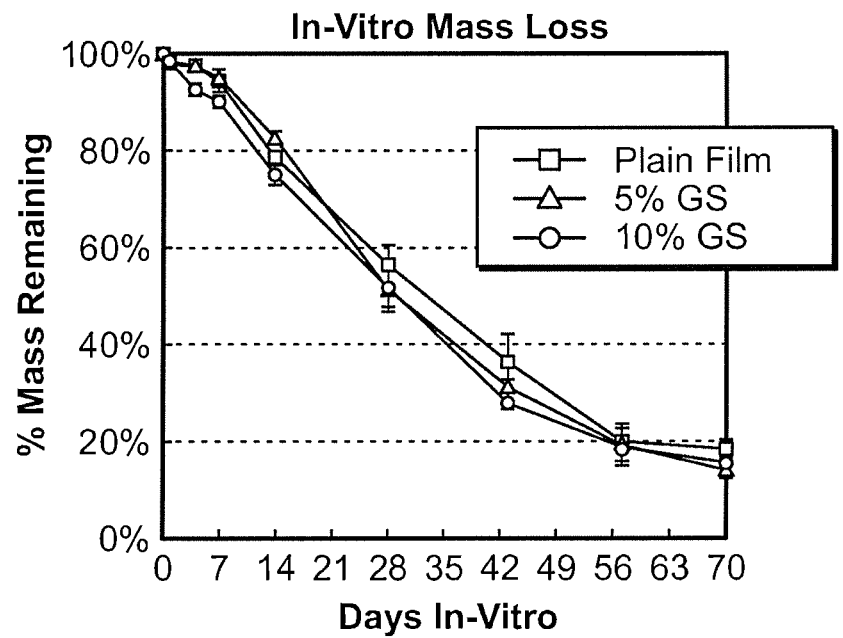
FIG. 15 is an in-vitro mass loss graph of a polymer film in accordance with an exemplary embodiment of the present invention.
Figure 16:
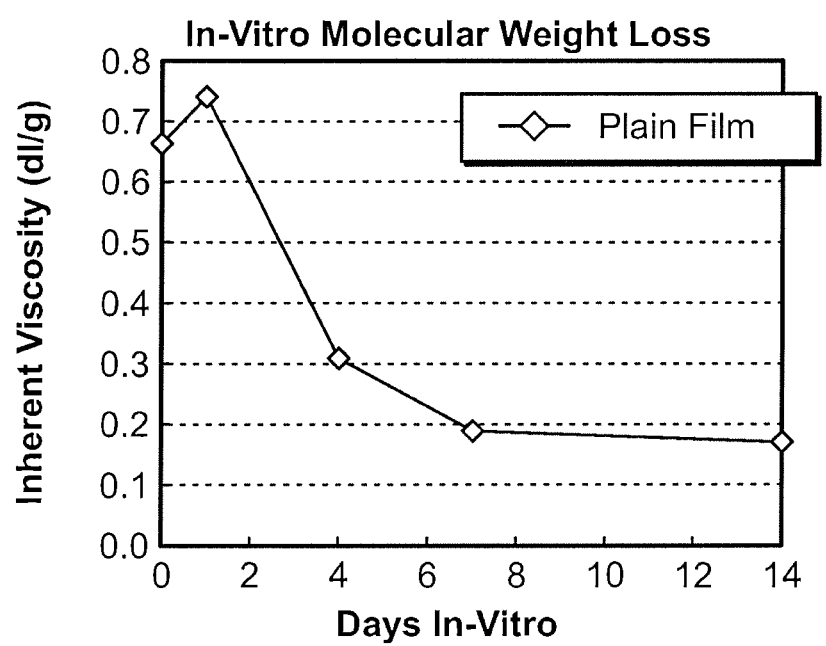
FIG. 16 is an in-vitro molecular weight loss graph of a polymer film in accordance with an exemplary embodiment of the present invention.

Referring to FIG. 11E, in one embodiment, apertures 14 have a diameter of approximately 0.75 mm and are spaced apart approximately 1.75 mm. In one embodiment, apertures 14 are arranged in a regular array (e.g., aligned rows and columns as illustrated in FIG. 11D). In one embodiment, apertures 14 are arranged in an irregular array.

Figure 4A:
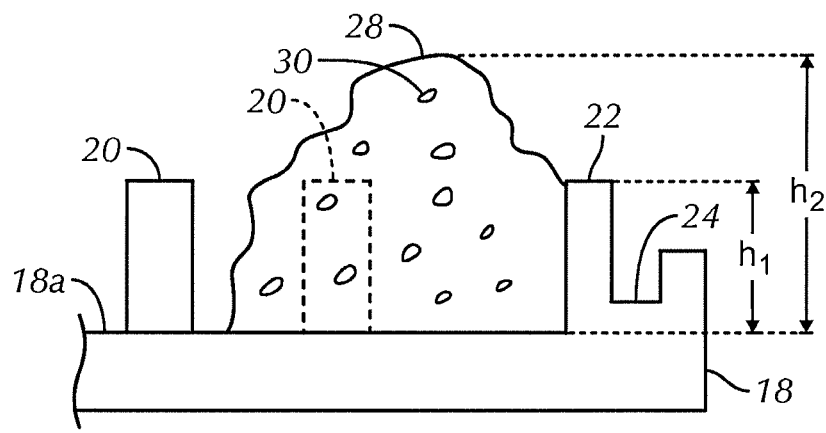
FIG. 4A is a schematic side cross-sectional view of the mold of FIG. 3A with the polymer added.
Figure 4B:
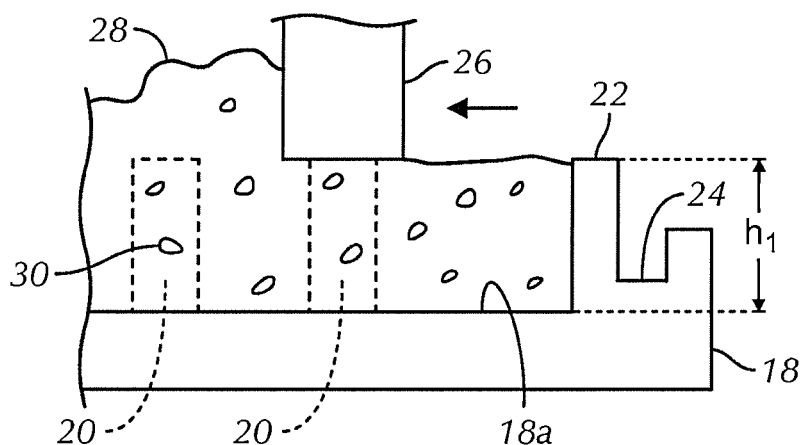
FIG. 4B is a schematic side cross-sectional view of the mold shown in FIG. 4A showing the drawing device drawing the polymer across the mold.
Figure 4C:
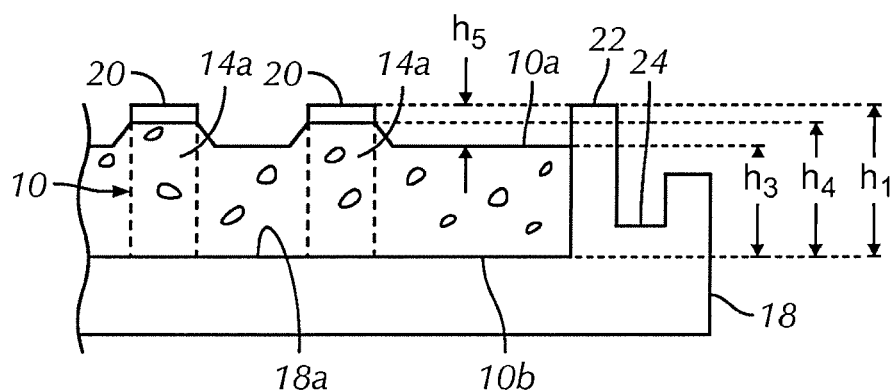
FIG. 4C is a schematic side cross-sectional view of the mold shown in FIG. 4A showing the polymer after being drawn across the mold and solidified to form a polymer film.

Referring to FIGS. 1A, 1B and 4C, in some embodiments, each aperture 14 is proximate to at least one raised lip 14a protruding from the first surface 10a. A benefit of the raised lip 14a around each perforation 14 may include providing a reinforcement or grommet to each perforation 14, effectively increasing the mechanical strength of film 10 relative to a similar perforated film with no raised lips 14a. A benefit of lips 14a may include a textured surface on first surface 10a. Such a texture may be an advantage for tactile feel or for the purpose of increasing (or reducing) friction of first surface 10a of film 10 when, for example, first surface 10a is in contact with another surface. In one embodiment, lip 14a decreases the tendency of the film 10 to adhere to a surface such as the metal surface of an implant, making it easier to slide a sleeve made from the film 10 onto the implant. In one embodiment, lips 14a act as stand-offs between the implant and film 10 reducing the surface area of film 10 that is in contact with the implant.

In one embodiment, first surface 10a includes a contiguous planar portion extending between the plurality of raised protruding lips 14a. In one embodiment, lip 14a is substantially in the shape of the outer surface of an impact crater. In one embodiment, lip 14a includes a continuous concave surface. In one embodiment, lip 14a includes a parabolic concave surface. In one embodiment, one or more of lips 14a (or, in some embodiments, each lip 14a) has a conave outer surface and an convex opposing inner surface, either or both of which are parabolic in shape. In one embodiment, lips 14a each have an edge that is raised above the contiguous planar portion of first surface 10a by approximately 0.1 mm to approximately 1.0 mm. In one embodiment, lips 14a each have an edge that is raised above the contiguous planar portion of first surface 10a by approximately 0.1 mm. In one embodiment, lips 14a each have an edge that is raised above the contiguous planar portion of first surface 10a by approximately 0.2 mm. In one embodiment, lips 14a each have an edge that is raised above the contiguous planar portion of first surface 10a by approximately 0.3 mm. In one embodiment, lips 14a each have an edge that is raised above the contiguous planar portion of first surface 10a by approximately 0.4 mm. In one embodiment, lips 14a each have an edge that is raised above the contiguous planar portion of first surface 10a by approximately 0.5 mm. In one embodiment, lips 14a each have an edge that is raised above the contiguous planar portion of first surface 10a by approximately 0.6 mm. In one embodiment, lips 14a each have an edge that is raised above the contiguous planar portion of first surface 10a by approximately 0.7 mm. In one embodiment, lips 14a each have an edge that is raised above the contiguous planar portion of first surface 10a by approximately 0.8 mm. In one embodiment, lips 14a each have an edge that is raised above the contiguous planar portion of first surface 10a by approximately 0.9 mm. In one embodiment, lips 14a each have an edge that is raised above the contiguous planar portion of first surface 10a by approximately 1.0 mm.

In one embodiment, due to lips 14a, first surface 10a has a first tactile feel that is different (e.g., distinguishable by a surgeon wearing a surgical glove) from a second tactile feel of second surface 10b without lips 14a. In one embodiment, apertures 14 in one or more areas on first surface 10a each are bounded by a raised lip 14a and apertures 14 in one or more other areas on first surface 10a are not so bounded. In one embodiment, height $h_4$ (see FIG. 4C) of each raised lip 14a is uniform. In one embodiment, at least one raised lip 14a has a different height $h_4$ than at least one other lip 14a. In one embodiment, one or more apertures 14 are bounded by a lip 14a on one or both first surface 10a and second surface 10b. An embodiment such as the one illustrated in FIG. 1A, may include a single continuous lip 14a that surrounds each aperture 14. The continuous lip may be substantially uniform in thickness and/or substantially uniform in height relative to any one aperture, or from aperture to aperture. Apertures 14 may be evenly spaced apart across all or at least a portion of the polymer sheet. In other embodiments, at least a portion of the polymer sheet is characterized by apertures that are spaced apart in at least two different spacing configurations.

In some embodiments, film 10 includes one or more drugs or other substance for delivery in the body. Such drugs include, but are not limited to, antimicrobial agents, antifibrotic agents, anesthetics and anti-inflammatory agents as well as other classes of drugs, including biological agents such as proteins, growth inhibitors and the like.

In one embodiment, film 10 includes an antibiotic. The antibiotic selected may be active against the majority of bacteria found in orthopedic implant related infections. These include primarily staphylococci, and Gram negative bacilli.

In one embodiment, the drug selected must be stable during the manufacturing processes required to fabricate the implant. In one embodiment, film 10 includes gentamicin. Gentamicin sulfate is thermally stable above 100° C., and is stable to organic solvents including DMSO, which is used in the manufacturing process in some embodiments.

Referring to FIGS. 4A-4C, in one embodiment, film 10 comprises a plurality of discrete eluting drug components 30. In one embodiment, film 10 is configured to elute the plurality of discrete drug components 30 at different time periods following implantation. In one embodiment, the elution of gentamicin in vive is a two-phase process, with a burst release occurring as soon as film 10 contacts water or body fluid, and a second phase which is controlled by the degradation rate of the polymer. In some embodiments, it is desirable to have an initial burst release of gentamicin to reduce bacterial contamination of the wound site on initial implantation, then a lower level release of gentamicin for a period of days to weeks afterward, to prevent growth of any surviving bacteria. In one embodiment, film 10 is configured to elute up to approximately 60 percent of the drug contained within film 10 approximately 1 week after film 10 has been implanted in contact with living tissue. In one embodiment, the combination of particle size and polymer degradation rate control the drug release profile, and create the desired 2-phase release. In one embodiment, the drug is released over a 2 to 3 week time period. In other embodiments, the drug is released over a shorter or longer time frame.

In one embodiment, the relative amounts of drug released during these two phases are controlled by the particle size. In one embodiment, drug components 30 are evenly distributed throughout film 10, and any drug components 30 in contact with a surface of film 10 are dissolved more rapidly than a drug component 30 that is not in contact with a surface of film 10. In one embodiment, a quantity of drug components 30 that are in contact with a surface of film 10 upon implantation are configured to release in a burst upon implantation. In one embodiment, the larger the size of drug components 30, the higher the proportion of drug components 30 in contact with the surface, and the greater the burst release. For this reason, the size of drug components 30, in one embodiment, is kept under 10 microns in diameter which reduces the burst release to approximately 20 to 35% of the total drug content. In one embodiment, drug components 30 are under 20 microns in diameter.

In one embodiment, film 10 is configured to deliver multiple drugs from one or more independent layers, some of which may contain no drug. In another embodiment, film 10 may include a plurality of drug components each being characterized by a different release rate from film 10 such that a first drug is associated with a first release profile that is different from a second release profile of a second drug.

Referring to FIGS. 3A-11F, there are shown devices used in a method of manufacturing films 10 in accordance with exemplary embodiments of the present invention.

In one embodiment, the manufacturing method of polymer films 10 was developed to make polymer films 10 for use as drug delivery membranes. In one embodiment, film 10 is solvent cast. In some embodiments, solvent casting methods are advantageous in the fabrication of films 10 that contain a drug component 30 that could be potentially damaged by the heat and shear of melt processes such as blown film extrusion. Producing films using a punch press (e.g., with many hundreds or thousands of holes or holes with complicated geometry) may also be time consuming and expensive. In some embodiments, a solvent and drug 30 are first mixed to form a well distributed suspension then polymer is added into the solution.

In some embodiments, methods described here allow for formation of the thin films 10 and formation of apertures 14 in a single step. In some embodiments, methods described herein allow for a film 10 with thousands of apertures 14 with accurate control of geometry and placement and accurate control of film thickness.

Referring to FIGS. 3A-3G, in some embodiments, film 10 is cast using mold 18. In one embodiment, mold 18 includes a plurality of protrusions or posts 20 extending from a bottom 18a of mold 18 to form apertures 14. In one embodiment, mold 18 is comprised of injection molded polypropylene. The mold may be manufactured from other materials, including polymers (see FIG. 3F), glass, metals (see FIG. 3O) or ceramics. In one embodiment, mold 18 is comprised of two or more materials. For example, mold 18 may have a base made from metal with a polymer coating to reduce adhesion of the cast film to the mold and/or to form posts 20. The cavity in the mold may be formed by a casting process, a compressing molding process, an injection molding process, a chemical etching process or a machining process.

In one embodiment, mold 18 includes a cavity depth of approximately 0.25 mm. In one embodiment, a distance from the bottom of the mold 18a to a top of each of the plurality of posts 20 is equal to the cavity depth (i.e., the height of peripheral wall 22) or vice versa. In one embodiment, posts 20 are longer than the desired thickness of film 10. In one embodiment, posts 20 extend 0.3 mm from the bottom of mold 18a. In one embodiment, posts 20 extend 0.2 mm from the bottom of mold 18a. In one embodiment, posts 20 extend 0.25 mm from the bottom of mold 18a. In one embodiment, posts 20 extend 0.3 mm from the bottom of mold 18a. In one embodiment, posts 20 extend 0.35 mm from the bottom of mold 18a. In one embodiment, posts 20 extend 0.4 mm from the bottom of mold 18a. In one embodiment, posts 20 extend 0.45 mm from the bottom of mold 18a. In one embodiment, posts 20 extend 0.5 mm from the bottom of mold 18a.

In one embodiment, posts 20 are arranged to produce the selected size, shape, pattern, and arrangement of apertures 14 described above. In one embodiment, a perimeter form or peripheral wall 22 defines a total mold area, and the plurality of posts 20 define an area that is substantially equal to or corresponding to the open pore area of film 10.

In one embodiment, mold 18 includes a trough 24 that extends at least partially around peripheral wall 22 of mold 18. In one embodiment, trough 24 extends around the entire peripheral wall 22 of mold 18. In some embodiments, trough 24 retains any excess polymer that flows or is urged over peripheral wall 22. In one embodiment, mold 18 includes an extension 40 extending laterally from at least one outer edge of mold 18. In one embodiment, extension 40 is provided for grasping and manipulating mold 18 without contacting the polymer solution within mold 18.

In one embodiment, a polymer solution 28 for adding to mold 18 is formed. In one embodiment, a polymer material is dissolved at a 4:1 solvent to polymer ration in dimethyl sulfoxide (DMSO) at elevated temperature and the drug gentamicin sulfate is added at 13% by weight. In one embodiment, polymer solution 28 is formed by introducing drug units 30 to a polymer/solvent blend at a temperature below 90° C. In one embodiment, polymer solution 28 comprises a cross-linkable pre-polymer such as polyurethanes, polyfumarates, polymethacrylates, etc.

Figure 6:
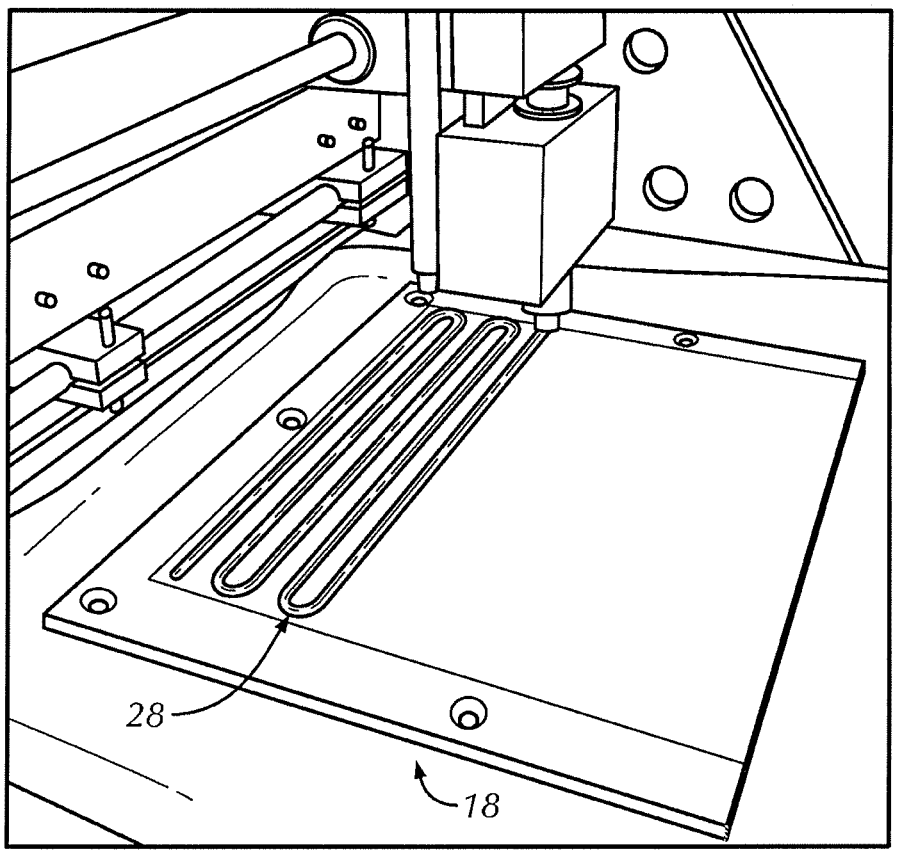
FIG. 6 is a perspective view of the automated casting apparatus of FIG. 5 showing the polymer being added to the mold.
Figure 8:
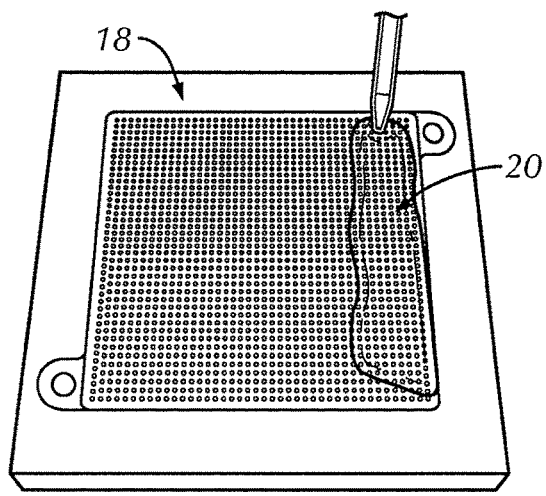
FIG. 8 is a perspective view of polymer being added to a mold in accordance with another exemplary embodiment of the present invention.

Referring to FIGS. 4A, 6 and 8, once the polymer solution 28 is prepared, polymer solution 28 is placed into a one sided mold 18. In some embodiments, the viscosity of polymer solution 28 and/or the density of posts 20 substantially inhibits the unaided flow of the polymer 28 throughout mold 18. In one embodiment, after adding polymer solution 28 to mold 18, the top surface of polymer solution 28 is a height $h_2$ above the base 18a of mold 18 which is greater than a height $h_1$ of the mold cavity and posts 20.

Figure 7:
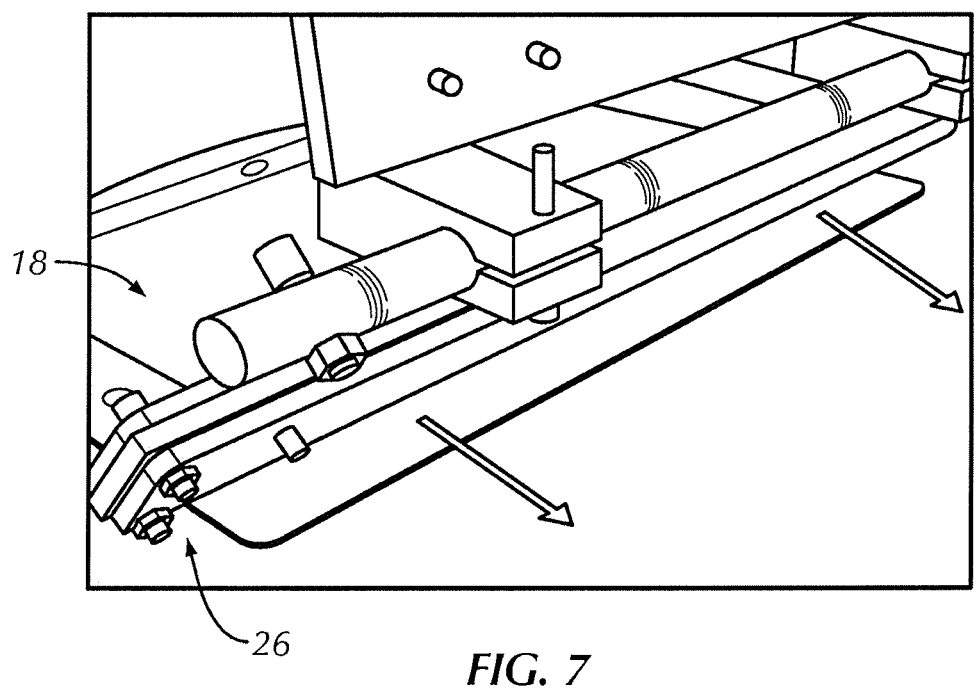
FIG. 7 is a perspective view of the automated casting apparatus of FIG. 5 showing the drawing device drawing the polymer across the mold.
Figure 9:
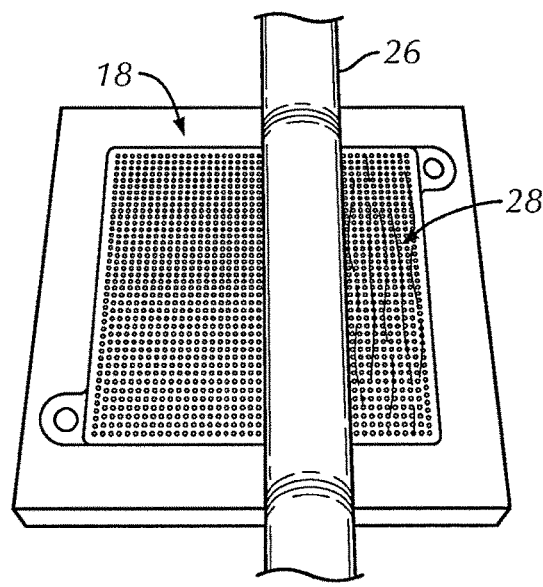
FIG. 9 is a perspective view of the mold of FIG. 8 showing the drawing device drawing the polymer across the mold.

Referring to FIGS. 4B, 7 and 9, after adding polymer solution 28 to mold 18, in one embodiment, an urging means 26 is used to urge the polymer solution around each of the plurality of posts 20. In one embodiment, urging means 26 includes a blade, bar, squeegee or roller that is slide, or the mold 18 is moved relative to urging means 26, across perimeter form 22 and the tops of posts 20 to force polymer solution 28 to flow around posts 20 and throughout mold 18 such that polymer solution 28 has a substantially uniform thickness. In one embodiment, drawing urging means 26 across mold 18 removes excess material from the top surface of posts 20. In one embodiment, an outer surface of each post 20 is substantially free of polymer solution 28 after the drawing.

Referring to FIG. 4C, once polymer solution 28 is drawn or spread throughout mold 18, polymer solution 28 is solidified to form film 10. In one embodiment, mold 18 is placed into a solvent drying oven at an elevated temperature to remove the solvent, leaving behind a thin cast film. In one embodiment, polymer solution 28 is solidified by cross-linking the polymer by applying UV radiation, temperature change, polymerization catalysts, soluble crosslinking agents or combinations thereof to polymer solution 28. In one embodiment, the solidifying step includes exposing mold 18 containing polymer solution 28 to a second solvent. In one embodiment where, for example, polymer solution 28 includes polymer, a drug and a first solvent, the first solvent is soluble in the second solvent, but the polymer and drug component are not soluble in the second solvent. Thus, by exposing polymer solution 28 to the second solvent, the first solvent is removed from the polymer solution leaving the polymer and the drug product to solidify to form, for example, the film.

In one embodiment, solidifying the polymer solution reduces a thickness of the polymer solution from a thickness $h_1$ to a thickness $h_3$. In one embodiment, solidifying the polymer solution reduces a thickness of the polymer solution proximate posts 20 from a thickness $h_1$ to a thickness $h_4$. In one embodiment, thickness $h_4$ of film 10 proximate posts 20 is greater than a thickness $h_1$ of film 10 between posts 20. In one embodiment, lips 14a are formed by polymer solution forming a meniscus around each of posts 20 during solidifying of polymer solution 28 to film 10. In one embodiment, meniscus or lip 14a is approximately the same height $h_4$ as height or depth $h_1$ of the mold 18. In one embodiment, height $h_4$ of lips 14a may be controlled by careful selection of the material and geometry of posts 20 or by coating posts 20 with, for example, a lubricious material such as a fluoropolymer or silicone mold release. In one embodiment, height $h_4$ of lips 14a is controlled by the concentration of the polymer solution.

Figure 10:
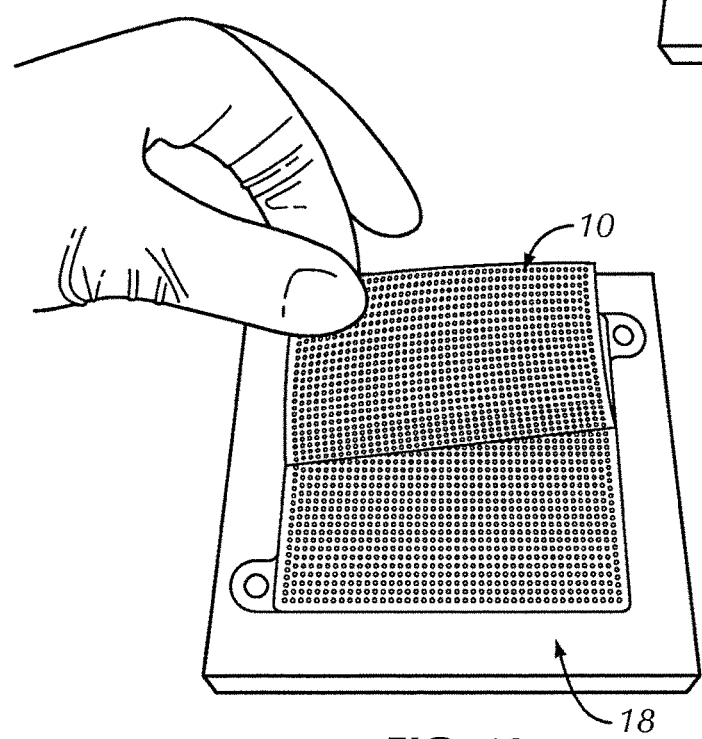
FIG. 10 is a perspective view of the mold of FIG. 8 showing the polymer film being removed from the mold.

Referring to FIG. 10, once polymer solution 28 is solidified, mold 18 and film are removed from the oven, allowed to cool, and the cast perforated film 10 is peeled out of mold 18.

Figure 5:
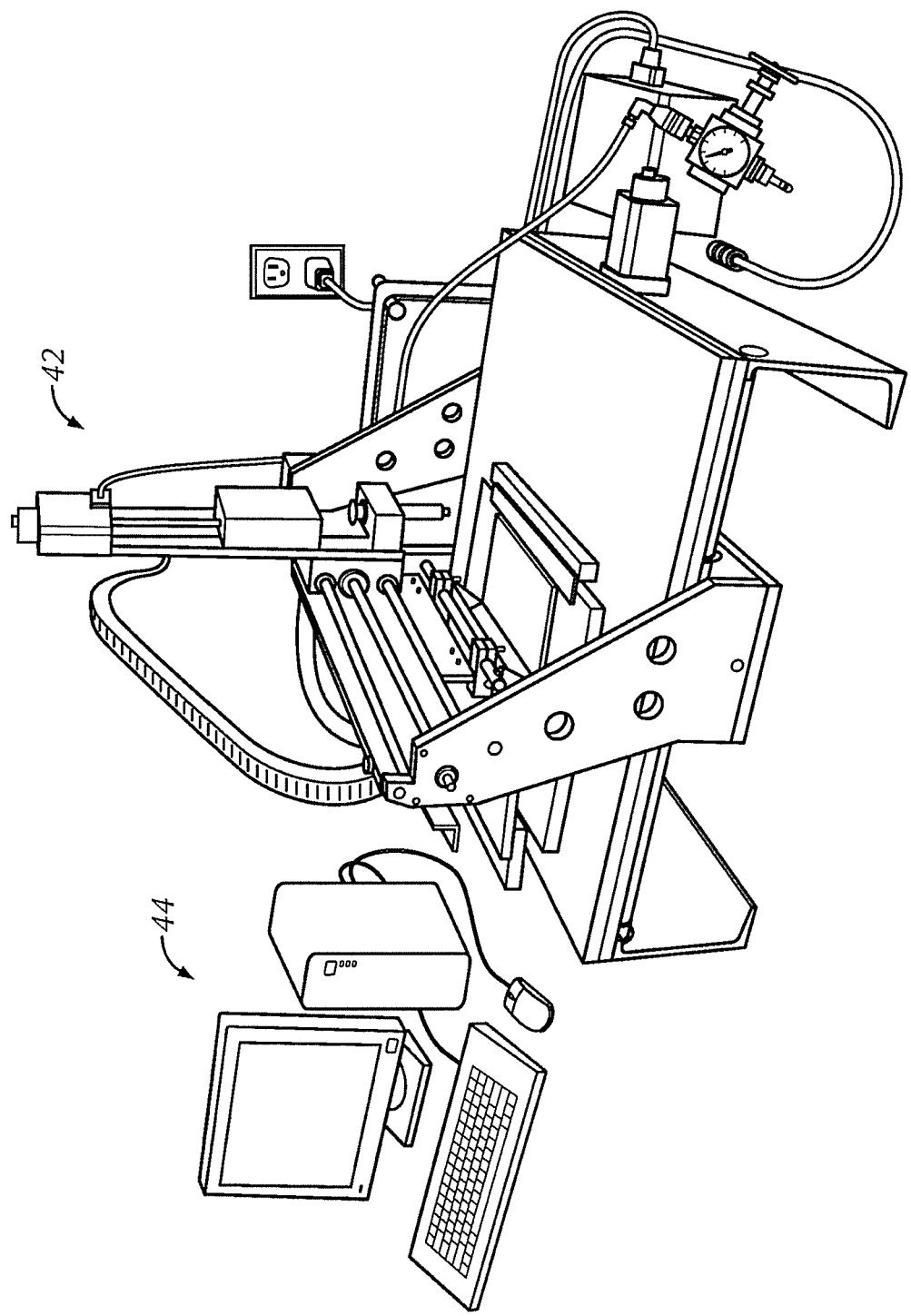
FIG. 5 is a perspective view of an automated casting apparatus in accordance with an exemplary embodiment of the present invention.

Referring to FIGS. 5-7, a method of producing film 10 may include an automated or partially automated casting machine 42. In one embodiment, the automated casting apparatus includes one or more computers 44 having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a computer readable storage medium having stored thereon computer-executable instructions which, when executed by a processor, perform one or more of the methods disclosed herein.

Film 10 may be manufactured by alternative methods. In one embodiment, polymer solution 28 can be cast onto perforated film material with a backing blotter layer, then the perforated film is removed from the blotter layer, removing the cast solution where there were holes in the casting sheet. One difference with such a process from the above described processes is that, in some embodiments, it does not create a raised lip around apertures 14.

In another embodiment, porous films may also be formed by a lyophilazation or freeze-drying method. In one embodiment, a thin solid film of polymer solution is cast in a mold, then the mold chilled to a temperature below the freezing point of the solution, then placed under vacuum to remove the solvent from the film. In some embodiments, this process will also produce fine pores which are much smaller than those described in some of the embodiments above.

In one embodiment, the polymer material used to form the cast film could be a crosslinkable prepolymer liquid, which is cast into the film mold as described, squeegeed to fill the mold and remove excess material, then crosslinked in place by UV radiation, temperature, a catalyst or other means. In one embodiment, this process could produce a very similar final product as described above, except that the final thickness of the cast film would be close to or the same as the depth of the mold, and there would be little or no meniscus or lip 14a around apertures 14.

In another embodiment, a thin porous film can be formed by a screen printing process. In one embodiment, a layer of solution is screen printed in the final pattern, then dried. In one embodiment, this produces a much thinner layer, however multiple layers of polymer can be screen printed and dried one on top of the other to build up the desired thickness of film.

In another embodiment, a similar casting process could be performed as described above using a glass plate with a pattern made from a hydrophobic polymer such as silicone, in the shape of the desired perforations. In one embodiment, when a thin layer of polymer solution is cast onto the plate, the surface tension differences between the glass and the patterned polymer cause the solution to concentrate on the glass surface, and pull away from the patterned hydrophobic polymer surface. In one embodiment, the solution is then dried to form a solid film with perforations in the same pattern as the silicone polymer. In one embodiment, this process could also be performed with a crosslinkable prepolymer liquid as described above.

In another embodiment, a thin porous polymer film is made using a two-sided mold, where the polymer solvent solution is injected into the mold, and chilled to solidify the solution. In one embodiment, the mold is then opened and one side removed, leaving the chilled solution in the cavity side. In one embodiment, the chilled solution side is placed into an oven to dry the polymer solution and form a film 10.

Referring to FIGS. 2 and 11A-11D, after creating film 10, film 10 is shaped and fashioned into a desired form. In one embodiment, film 10 is shaped and fashioned to generally match the size and shape of medical device 12. In some embodiments, film 10 is shaped and fashioned into a sheath or sleeve 32, 34, 36, 38.

Referring to FIGS. 11A-11F, sleeve 32, 34, 36, 38 includes at least one seam 16 configured to form film 10 into a sheath. In one embodiment, sleeve 32, 34, 36, 38 is formed by attached a first film 10 to a second film 10 around the outer periphery. In one embodiment, film 10 is folded and at least partially secured to itself. For example, film 10 may be shaped into a cylinder to adjoin two opposing edges. In one embodiment, second surface 10b is overlapped with first surface 10a to form seam 16. In one embodiment, second surface 10b is overlapped with second surface 10b to form seam 16. In one embodiment, seam 16 is secured by heating the overlapping portions of film 10 and allowing to re-solidify. In one embodiment, both ends of sleeve 32, 34, 36, 38 are left open for insertion of medical device 12. In one embodiment, one or more ends are closed. In one embodiment, polymer sheet is first to the desired size and shape before forming sleeve 32, 34, 36, 38.

In addition to sleeves 32, 34, 36, 38, film 10 may be used, in some embodiments, for other medical applications such as hernia repair mesh, adhesion barrier, soft tissue augmentation, filtration membranes, drug delivery membranes, bone graft containment (e.g., for maintaining bone graft in place for example in a spinal fusion procedure, or segmental defect grafting in a long bone), or wound care products such as bandages.

Example 1

In one exemplary embodiment, implants were tested by implantation in sheep. The implants were metal plates with tubular, thin (0.05-0.08 mm), transparent polymer sleeves carefully slipped over the metal plates just before they were surgically inserted and attached to the bone. The sleeves had a tight fit, covered the metal plates completely over the entire length, although they were open at both ends of the plates. The sleeves were comprised of a synthetic copolyester (glycolide, caprolactone, trimethylenecarbonate, lactide) with perforation holes of 1.5 mm diameter equally spaced throughout. One group of sleeves contained triclosan (2,4,4'-trichloro-2'-hydroxydiphenyl ether) at a concentration of 1%, one group of sleeves contained gentamicin at a concentration of 10%, and one group of sleeves contained a combination of both triclosan (1%) and gentamicin (10%). The concentration of gentamicin and Triclosan were chosen based on in vitro testing to determine the therapeutic window for each compound.

The hydrophobic triclosan was in complete solution within the polymer, in contrast to the hydrophilic gentamicin, which remained suspended as 10-20 μm small particles. In vitro testing has shown that due to its poor water solubility, triclosan is released from these films only slowly over a to 3 weeks period, with minimal initial burst release.

Approximately 50% of the more water soluble gentamicin which is exposed to the surface of the sleeves was released into the adjacent tissue within 24 hours after insertion. The remaining gentamicin encapsulated in the depth of the polymer dissolves more slowly and was released over a 2 to 3 week period after implantation. The polymer was designed to degrade through hydrolysis within 60 days after surgery.

The sleeves with or without antimicrobial agents were proven biocompatible, with minimal effect on soft tissue and bone healing and not corrosive to the metallic implants. Additional details of the experiment can be found in Vet Surg. 2012 Jan. 12. *Biodegradable Sleeves for Metal Implants to Prevent Implant-Associated Infection: An Experimental In Vivo Study in Sheep*. Von Plocki S C, Armbruster D, Klein K, Kämpf K, Zlinszky K, Hilbe M, Kronen P, Gruskin E, von Rechenberg B., which is hereby incorporated by reference in its entirety.

Example 2

In one exemplary embodiment, film 10 is manufactured by the following method:

Determination of Gentamicin Moisture Content:

The moisture content of gentamicin sulfate powder is measured by a loss on drying method. Approximately 0.5 grams of gentamicin is weighed in a glass jar, then heated under vacuum to 110° C. for 3 hours and weighed a second time. The weight loss is recorded as the moisture content, which is used to calculate the percent moisture.

Solution Mixing:

14.69 grams of gentamicin sulfate powder is weighed, compensating for the percent moisture content as calculated above. This is mixed into 400 g of DMSO solvent in a 1 L vessel, using a paddle mixer. The mixture is stirred for 30 minutes until the gentamicin is uniformly distributed. 100 g of a copolymer containing glycolic acid, caprolactone, lactic acid, and trimethylene carbonate monomers is added to the suspension, and the mixing vessel is heated to 65° C. Mixing is continued for 2 hours until the polymer is completely dissolved into the solution, then the solution temperature is reduced to 55° C.

Film Casting & Solvent Drying:

A casting mold and drawing blade made from high density polyethylene are used to cast thin perforated films from the polymer solution. The casting mold and drawing blade are pre-cleaned using an alkaline detergent solution and loaded into an automated CNC casting fixture. 15 ml of the polymer solution are drawn up in a polypropylene syringe, which is loaded into the casting fixture. The casting fixture automatically dispenses the solution onto the casting mold, and draws the blade across the surface of the mold. The mold filled with polymer solution is placed into a solvent drying oven at 85° C. for approximately 90 minutes to dry the film. The molds are removed from the drying oven and the films are peeled from the molds within 2 minutes.

Sleeve Sealing:

An impulse heat sealing press with specially shaped dies is used to seal and cut the cast film into the shape of a sleeve. Two cast films are placed into the press, and the press is closed with a pressure of 80 psi and heated to 200° C. for 4 seconds. The sleeves are removed from the excess film material and cut to the appropriate length. Sealed sleeves can be dried under vacuum at 50° C. and sealed in moisture barrier packaging to prevent degradation of the bioabsorbable polymer.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed:

1. A method of producing an implantable drug eluting polymer film comprising:
   preparing a polymer solution including a solvent, a biologically compatible polymer, and a water-soluble antimicrobial or antibiotic drug, wherein the drug is suspended in the polymer solution as discrete drug particles having an average particle diameter of under 20 microns or smaller;
   placing the polymer solution containing the discrete drug particles into a one-sided mold having a plurality of protrusions extending from a bottom of the mold wherein the polymer solution is characterized by a viscosity that inhibits the unaided flow of the polymer throughout the mold;
   urging the polymer solution around each of the plurality of protrusions; and
   solidifying the polymer solution into an implantable polymer film, wherein during solidifying of the polymer solution into the film, the polymer solution forms a raised meniscus around each of the plurality of protrusion and a plurality of raised lips are formed in the film around each of the plurality of protrusion from solidification of the raised meniscus such that the raised lips each surround an aperture in the film formed from each of the plurality of protrusions and wherein the polymer film is configured to release the discrete drug particles in a two-phase release profile including an initial burst release of the portion of the discrete drug particles exposed at a surface at a surface of the polymer film.

2. The method of claim 1, wherein the mold includes a perimeter form extending to an elevation that is substantially equal to an elevation of each of the plurality of protrusions.

3. The method of claim 2, wherein the urging comprises drawing a urging means across the perimeter form and the plurality of protrusions to force the polymer solution to flow around the plurality of protrusions and throughout the mold such that the polymer solution has a substantially uniform thickness.

4. The method of claim 3, wherein an outer surface of each of the protrusions is substantially free of polymer solution after the drawing.

5. The method of claim 2, wherein the placing step includes depositing the polymer solution in the mold such that a portion of the polymer solution is above the elevation of the perimeter form and the protrusions.

6. The method of claim 1, wherein the polymer solution is formed by combining a solvent, a polymer, and the drug at a temperature below 90° C.

7. The method of claim 1, wherein solidifying the polymer solution includes reducing a thickness of the polymer solution.

8. The method of claim 1, wherein a distance from the bottom of the mold to a top of each of the plurality of protrusions is less than approximately 0.3 mm.

9. The method of claim 1, wherein the perimeter form defines a total mold area and the plurality of protrusions define an area that is at least about 15% of the total mold area.

10. The method of claim 1, further comprising peeling the drug eluting film from the mold.

11. The method of claim 1 wherein the polymer solution comprises a cross-linkable pre-polymer solution.

12. The method of claim 1, wherein the solidifying step includes cross-linking the polymer by applying UV radiation, temperature change, polymerization catalysts, soluble cross-linking agents or combinations thereof to the polymer solution.

13. The method of claim 1, wherein the polymer solution comprises a first solvent and a polymer and the solidifying step includes exposing the polymer solution to a second solvent in which the first solvent is soluble and in which the polymer and the drug are not soluble such that the first solvent is at least substantially removed from the polymer solution and the polymer solidifies to contain the drug.

14. The method of claim 1, wherein the discrete drug particles have an average particle diameter in the range of about 10 microns to about 20 microns.

15. The method of claim 1, wherein the discrete drug particles have an average particle diameter of under 10 microns or smaller.

16. The method of claim 1, wherein the solidifying step comprises exposing a portion of the discrete drug particles at a surface of the polymer film.

17. The method of claim 1, wherein the discrete drug particles comprise about 10% to about 13% by weight of the total weight of the polymer film.

18. The method of claim 1, wherein the polymer solution includes a second drug.

19. The method of claim 18, wherein the second drug is soluble in the polymer solution.

20. The method of claim 19, wherein the second drug is an antimicrobial or antibiotic agent.

21. The method of claim 1, wherein solidifying the polymer solution forms a polymer film defining a first surface and a second surface and a continuous planar portion extending along the first surface between the plurality of raised lips, the continuous planar portion having an average thickness between the first surface and the second surface in the range of approximately 0.05 mm to approximately 0.50 mm, and wherein the plurality of raised lips have a height measured above the continuous planar portion in the range of 0.1 mm to approximately 1.0 mm.

* * * * *